(12) United States Patent
Raby et al.

(10) Patent No.: US 8,562,339 B2
(45) Date of Patent: Oct. 22, 2013

(54) DIGITAL ORTHODONTIC APPLIANCE COUPLING MATRIX

(75) Inventors: Richard E. Raby, North St. Paul, MN (US); Oliver L. Puttler, La Crescenta, CA (US); Nicholas A. Stark, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1399 days.

(21) Appl. No.: 11/777,350

(22) Filed: Jul. 13, 2007

(65) Prior Publication Data

US 2009/0017410 A1  Jan. 15, 2009

(51) Int. Cl.
*A61C 3/00* (2006.01)

(52) U.S. Cl.
USPC .......................................................... 433/24

(58) Field of Classification Search
USPC ................................................... 433/24, 213
See application file for complete search history.

(56) References Cited

U.S. PATENT DOCUMENTS

| | | | |
|---|---|---|---|
| 5,011,405 A | 4/1991 | Lemchen | |
| 5,474,448 A | 12/1995 | Andreiko et al. | |
| 6,123,544 A | 9/2000 | Cleary | |
| 6,224,373 B1 * | 5/2001 | Lee et al. | 433/172 |
| 6,334,853 B1 | 1/2002 | Kopelman et al. | |
| 6,554,613 B1 | 4/2003 | Sachdeva et al. | |
| 6,776,614 B2 | 8/2004 | Wiechmann et al. | |
| 6,971,873 B2 | 12/2005 | Sachdeva et al. | |
| 7,125,249 B1 | 10/2006 | Lauren | |
| 7,210,929 B2 | 5/2007 | Raby et al | |
| 2002/0010568 A1 | 1/2002 | Rubbert et al. | |
| 2004/0265770 A1 | 12/2004 | Chapoulaud et al. | |
| 2005/0170309 A1 | 8/2005 | Raby et al. | |
| 2005/0208450 A1 * | 9/2005 | Sachdeva et al. | 433/24 |
| 2005/0244790 A1 | 11/2005 | Kuperman | |
| 2006/0024637 A1 | 2/2006 | Raby et al. | |
| 2006/0073436 A1 | 4/2006 | Raby et al. | |
| 2006/0078842 A1 * | 4/2006 | Sachdeva et al. | 433/24 |
| 2007/0087302 A1 | 4/2007 | Reising et al. | |
| 2007/0099146 A1 | 5/2007 | Reising | |
| 2007/0238064 A1 | 10/2007 | Stark et al. | |

OTHER PUBLICATIONS

U.S. Appl. No. 11/689,869, "Methods and Assemblies for Making an Orthodontic Bonding Tray Using Rapid Prototyping," filed Mar. 22, 2007.
U.S. App. No. 11/551,372, "Digital Orthodontic Treatment Planning," filed Oct. 20, 2006.

* cited by examiner

*Primary Examiner* — Robyn Doan
*Assistant Examiner* — Matthew Nelson

(57) ABSTRACT

A digital orthodontic treatment planning system provides a practitioner with digital representations of at least a part of a tooth of a patient and at least part of a coupling matrix within a three-dimensional environment. By interacting with the system, orthodontic practitioners are able to visualize a coupling matrix that results from a specific orthodontic appliance position relative to a tooth of the patient's dental arch. The digital representation of the coupling matrix represents a substance, such as a cured adhesive, that connects an orthodontic appliance to a tooth of a patient. The system determines a thickness of at least a portion of the coupling matrix. In one embodiment, the system indicates the total thickness via a thickness map, such as a color-coded thickness map. In another embodiment, the system indicates a deviation from a baseline thickness via a thickness map.

10 Claims, 10 Drawing Sheets

DIGITAL ORTHODONTIC APPLIANCE COUPLING MATRIX

TECHNICAL FIELD

The invention relates to orthodontics, and more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

A position of the bracket on a tooth as well as the interaction between the bracket and an archwire affects a resulting position of the tooth. As can be appreciated, it is important for the practitioner using straight wire appliances to precisely fix each bracket in the proper position on the corresponding tooth in order to achieve the desired tooth movement. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth often requires an orthodontic practitioner to visually determine the proper location of the brackets on the respective teeth based on an estimate of how the brackets will affect the movement of the teeth. One factor in selecting a type of bracket, or another orthodontic appliance, to use with a particular patient is the fit between the bracket and the surface of the patient's tooth to which the bracket is applied. A poor fit between a bracket and the tooth surface may result in a reduction in the strength of the bond between the bracket and tooth. A bracket is typically attached to a patient's tooth via an adhesive or another similar substance, which typically fills the space between the surface of the patient's tooth and the bracket. Once cured, the adhesive between the bracket and the tooth is sometimes referred to as an "adhesive layer," "custom base" or "adhesive pad," depending on the type of bonding technique that is employed (e.g., an indirect or direct bonding technique). However, if the cured adhesive is too thick or unevenly distributed, the bond strength may be compromised. Accordingly, the practitioner may determine that the bracket provides a poor fit for the particular patient.

The state of the art in orthodontics is rapidly moving toward digital and computer-aided techniques. These techniques include the use of intra and extra-oral scanners, three-dimensional (3D) modeling of a tooth structure, and fabrication of orthodontic appliances from digital data.

SUMMARY

In general, the invention relates to computer-implemented techniques for assisting practitioners in orthodontic diagnosis and treatment. More specifically, a computing system is described that provides a three-dimensional (3D) environment for modeling and depicting a digital representation of a patient's dental arch. By interacting with the system, an orthodontic practitioner is able to place one or more orthodontic appliances, such as brackets, within the 3D environment relative to the digital representation of the dental arch. The orthodontic practitioner may place the digital representations of the orthodontic appliances manually or with the aid of orthodontic appliance fitting algorithms implemented by the computing system. For at least one orthodontic appliance, the computing system provides a digital representation of a coupling matrix that results from the orthodontic appliance position relative to a respective tooth of the patient's dental arch. The digital representation of the coupling matrix represents a substance, such as a cured adhesive or machined base, that bonds, affixes or otherwise connects the orthodontic appliance to the tooth.

The digital representation of the coupling matrix presented by the computing system provides a useful tool for visualizing a relative position between a digital representation of an orthodontic appliance and a respective tooth of the modeled dental arch. Based on the configuration (e.g., the shape and size) of the coupling matrix, an orthodontic practitioner may determine whether the selected orthodontic appliance provides a satisfactory fit for the particular tooth of the particular patient, or whether the practitioner should select another orthodontic appliance. For example, the thickness (measured in a substantially labial-lingual direction) distribution of the coupling matrix may be indicative of the fit between the particular type of orthodontic appliance and the respective tooth of the patient. Because the surface of a particular patient's tooth is typically unique to the patient, it may be useful for the orthodontic practitioner to determine how a particular orthodontic appliance fits relative to the tooth of the particular patient within a virtual 3D environment prior to actually bonding the appliance to the tooth.

In some embodiments, the computing system indicates a thickness of one or more portions of the coupling matrix. For example, the computing system may generate a thickness map of the coupling matrix within the 3D environment. The thickness map may be presented as, for example, a color-coded map, where different colors represent different thickness ranges or different thickness deviations from a predetermined thickness or a contour map that includes contour lines to indicate a thickness of the coupling matrix. The predetermined thickness may be a norm thickness preferred by one or more practitioners or another predetermined thickness automatically selected by the computing system or manually selected by a practitioner.

The color-coded thickness map provides a visual reference for the orthodontic practitioner to relatively quickly ascertain the thickness distribution of the coupling matrix, as well as the fit between the respective orthodontic appliance and the respective surface of the patient's tooth to which the appliance is applied. In some cases, it may be desirable to balance the thickness of the coupling matrix about a center of the appliance in order to provide a better fit between the appliance and the tooth. In other cases, the orthodontic practitioner may purposefully define a coupling matrix with an imbalance in its thickness in order to achieve a certain result (e.g., a movement of the tooth in a certain direction).

In some embodiments, the computing system may indicate a volume of the coupling matrix. Alternatively, a practitioner may determine the volume based on the thickness map. If the coupling matrix is comprised of adhesive or another bonding material, the practitioner may utilize the volume information to determine the amount of adhesive to dispense when applying the orthodontic appliance directly to the tooth of the patient in a direct bonding technique or to a physical model of the tooth in an indirect bonding technique. The adhesive may be applied to the orthodontic appliance, the tooth or both.

In some modes of operation, the computing system displays a digital representation of the coupling matrix positioned between an orthodontic appliance and a tooth of the modeled dental arch within the 3D environment. In other modes of operation, the computing system displays a digital representation of the coupling matrix relative to a tooth of the modeled dental arch, and does not display the orthodontic appliance. In this way, the practitioner may control whether the digital representation of the orthodontic appliance is displayed.

In one embodiment, the invention is directed to a computer-implemented method that comprises rendering a digital representation of at least a portion of a tooth within a three-dimensional (3D) environment, determining a position of a digital representation of an orthodontic appliance relative to the digital representation of the tooth within the 3D environment, determining a thickness of at least a portion of a coupling matrix, and rendering a digital representation of a coupling matrix within the 3D environment based on the position of the digital representation of the orthodontic appliance.

In another embodiment, the invention is directed to a system comprising a computing device and modeling software executing on the computing device. The modeling software comprises a rendering engine that renders digital representations of at least a portion of a tooth and at least a portion of a coupling matrix within a 3D environment, an orthodontic appliance control module to automatically calculate a position of an orthodontic appliance relative to the digital representation of the tooth within the 3D environment, and a coupling matrix calculation module to determine a thickness of at least a portion of the coupling matrix based on the orthodontic appliance position.

In another embodiment, the invention is directed to a computer-readable medium containing instructions. The instructions cause a programmable processor to render a digital representation of at least a portion of a tooth within a three-dimensional (3D) environment, determine a position of a digital representation of an orthodontic appliance relative to the digital representation of the tooth within the 3D environment, determine a thickness of at least a portion of a coupling matrix, and render a digital representation of the coupling matrix within the 3D environment based on the position of the digital representation of the orthodontic appliance.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
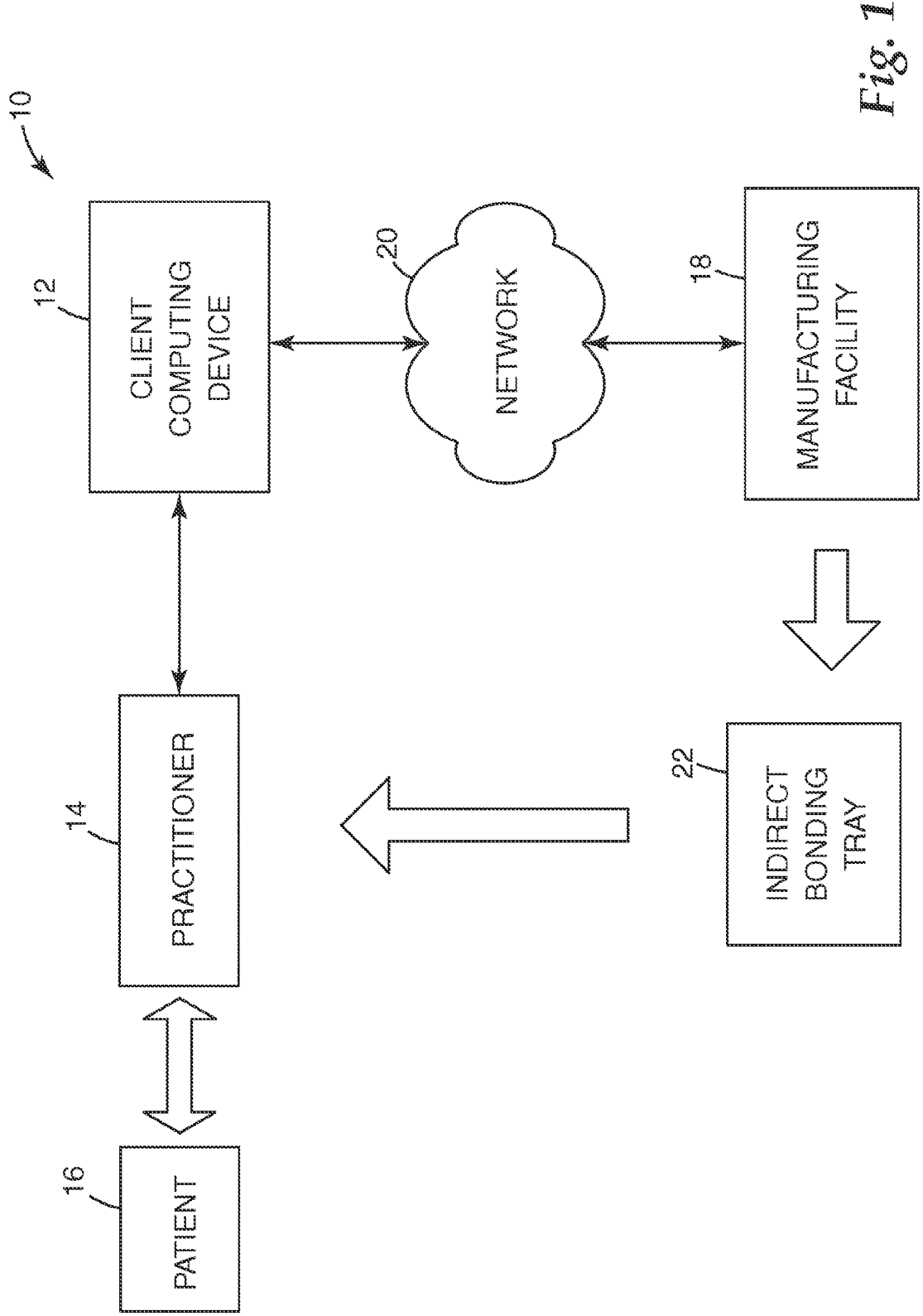
FIG. 1 is a block diagram illustrating an exemplary computer environment in which a client computing device receives an indication of a desired tooth position and/or desired tooth movement for generating an orthodontic treatment plan for a particular patient.

FIG. 1 is a block diagram illustrating an exemplary computer environment 10 in which client computing device 12 presents an environment for orthodontic practitioner 14 to interact with a digital representation of a portion of or an entire dental arch of patient 16 to generate and visualize an orthodontic treatment plan for patient 16. The orthodontic industry has developed standard prescriptions for many commercially available orthodontic appliances. In general, a prescription may set forth characteristics of one or more appliances, or a set of appliances. For example, the characteristics for a bracket may include torque, angulation, labial-lingual offset (in-out) and rotational offset. For some patients, a standardized set of metrics for the teeth in the dentition may satisfy the functional and aesthetic requirements. For other patients, practitioner 14 may create a customized prescription to achieve a more aesthetically pleasing result, or to more adequately take into account that patient's malocclusion. As another example, a combination of standardized and customized prescriptions for different teeth in the dentition may be used. Practitioner 14 may formulate a customized prescription using modeling software provided by client computing device 12.

As described herein, client computing device 12 provides an intuitive interface for practitioner 14 to realize an orthodontic treatment plan (e.g., bracket placement) for achieving desired tooth positions. In particular, client computing device 12 provides a user interface that displays digital representations of at least one tooth of a dental arch of the patient within a three-dimensional (3D) environment. Client computing device 12 may display a digital representation of a portion of or an entire dental arch of a patient. In some embodiments, client computing device 12 enables the practitioner to select a view of the dental arch for displaying, such as the entire dental arch, a portion of the dental arch, an occlusal view of the dental arch, a labial view of the dental arch, a lingual view of the dental arch, or other views.

The digital representation of the teeth may be initially generated by digitally scanning a physical dental impression of the teeth of patient 16, or by scanning a casting made from the impression. Alternatively, practitioner 14 may use an intraoral scanner to produce the digital representation directly from the teeth of patient 16. Other methods of scanning or otherwise obtaining a digital representation of the teeth are also possible.

Client computing device 12 also provides a user interface that displays a digital representation of an orthodontic appliance (i.e., a virtual orthodontic appliance) positioned relative to a tooth of the digital representation of the dental arch to which the orthodontic appliance is attached, and a digital representation of a coupling matrix (i.e., a virtual coupling matrix rendered within the 3D environment) between the tooth and the orthodontic appliance. Client computing device 12 implements modeling software that determines the orthodontic appliance position, which includes the linear position along the mesial-distal direction, labial-lingual direction, and occlusal-gingival direction, as well as the rotational orientation of the orthodontic appliance relative to a tooth.

The coupling matrix may be representative of a substance, such as an adhesive, that bonds, affixes or otherwise connects the orthodontic appliance to a surface of one or more teeth. The coupling matrix may also be a material that defines a base for the orthodontic appliance, where the base interfaces with a surface of one or more teeth to connect the appliance to the tooth, e.g., with the aid of an adhesive. For example, in some embodiments, the coupling matrix may be defined by a metal, polymer or other material that is integral or coupled to the appliance. In some embodiments, the base may be machined to define a surface that substantially corresponds to the surface of the tooth to which the appliance is applied based on the digital representation of the coupling matrix.

In a direct bonding technique, the coupling matrix is defined by an adhesive that is applied when the orthodontic appliance, such as a bracket, is applied directly to the tooth of the patient with the adhesive. Thus, in a direct bonding technique, the coupling matrix may define an "adhesive pad" for the orthodontic appliance. In some direct bonding techniques, the practitioner may manually place the orthodontic appliance onto one or more teeth of the patient In an indirect bonding technique, the coupling matrix is typically defined by an adhesive that is applied when the orthodontic appliance is applied to a physical model of the tooth of the patient. The physical model may be created via a molding technique, a stereo lithographic technique, other rapid prototyping techniques or another suitable technique. A mechanical device, such as a multiple axis "pick and place" robot may place the orthodontic appliances on the physical model of the patient's teeth under the control of computing device 12 or another computing device. Alternatively, a physical model may be provided with a guide structure to assist in guiding the appliances to desired positions on the model tooth, such as described in U.S. patent application Ser. No. 11/689,869, entitled, "METHODS AND ASSEMBLIES FOR MAKING AN ORTHODONTIC BONDING TRAY USING RAPID PROTOTYPING," which is incorporated herein by reference in its entirety, although other transfer trays may also be used. Examples of suitable transfer trays (also known as indirect bonding trays) are also described in U.S. Pat. No. 6,123,544, entitled, "METHOD AND APPARATUS FOR PRECISE BOND PLACEMENT OF ORTHODONTIC APPLIANCES," which issued on Sep. 26, 2000 and is incorporated herein by reference in its entirety. Other transfer trays may also be used.

In an indirect bonding technique, the coupling matrix provides a structure customized for mounting on the patient's tooth structure, such as by using a placement device (e.g., a transfer tray). Thus, in an indirect bonding technique, the custom matrix may define a "custom base" for the orthodontic appliance.

After determining the position of the orthodontic appliance relative to one or more teeth within the 3D environment presented by client computing device 12, a digital representation of the coupling matrix is rendered. The coupling matrix fills the defined space between the surface of the one or more teeth and the orthodontic appliance within the 3D environment. Thus, computing device 12 generates a digital representation of the coupling matrix after determining a position of the orthodontic appliance relative to a tooth within the 3D environment.

Computing device 12 may determine the position of the orthodontic appliance within the 3D environment, for example, using a bracket fitting algorithm and/or input from practitioner 14, as described in further detail below. The coupling matrix is then digitally represented as a 3D object within the 3D environment, where the 3D object substantially corresponds to the space between the surface of the orthodontic appliance facing a tooth, and the surface (e.g., facial or lingual surface) of the tooth. That is, in some embodiments, the digital representation of the coupling matrix has substantially the same shape and size as the gap between a respective orthodontic appliance and tooth within the 3D environment. For example, one surface of the coupling matrix may have substantially the same boundary and contours as the mating surface of the orthodontic appliance. An opposite surface of the coupling matrix may have substantially the same contour as a portion of the surface of the tooth to which the appliance is to be applied and a boundary that is defined by a projection of the appliance boundary onto the surface of the tooth.

In other embodiments, the digital representation of the coupling matrix has substantially the same shape and size as the gap between the orthodontic appliance and tooth, minus the space occupied by any additional material (such as an adhesive material) used to bond or otherwise connect the coupling matrix to the tooth surface. For example, in the case of some indirect bonding techniques, after the custom base is formed using the physical model of the patient's tooth, the custom base, along with the appliance to which it is attached, may be removed from the physical model and adhered to the patient's tooth with the aid of a primer. Accordingly, in some embodiments, modeling software of computing device 12 may model the primer in addition to the coupling matrix. The modeling software may account for the thickness of the primer in the digital representation of the custom base. However, in some indirect bonding techniques, a thickness of the primer may be substantially less than a thickness of the coupling matrix. Thus, in some embodiments, the modeling software does not display the primer or account for a thickness of the primer when considering a thickness of the coupling matrix.

In some indirect bonding techniques, a custom base includes a mold release agent layer that may be used to release the custom base from the physical model of the patient's teeth. It has been found that a thickness of the mold release agent is substantially similar to a thickness of the primer that is used to adhere or otherwise connect the custom base to the patient's actual tooth. Thus, in some embodiments, the modeling software of computing device 12 inherently accounts for the thickness of the primer in the digital representation of the custom base by including the mold release agent as part of the custom base. In some embodiments, the digital representation of the coupling matrix may be presented without displaying a digital representation of the orthodontic appliance.

In either the direct or indirect bonding techniques, a first side of the coupling matrix defines a contour that substantially conforms to the contour of the intended mounting location of the tooth to which the orthodontic appliance is attached. For example, if the orthodontic appliance is coupled to a facial surface of a patient's tooth, the coupling matrix may define a substantially concave contour that substantially conforms to the substantially convex contour of the facial surface of the tooth. A second side of the coupling matrix defines a contour that substantially corresponds to the contour of the surface of the orthodontic appliance intended to be facing the tooth of the patient. The contour of the surface of the orthodontic appliance may differ based on the type of orthodontic appliance.

The side walls of the digital representation of the coupling matrix that extend between the orthodontic appliance and the tooth may define a substantially cylindrical surface (i.e., having substantially parallel side walls) or a curved surface, such as a convex or concave surface. For example, in some indirect and direct bonding techniques, excess coupling matrix material that does not sit between the tooth and orthodontic appliance after the appliance is attached to the tooth may be removed. The excess coupling matrix material may be referred to as "flash." Examples of flash removal techniques include the use of a scaler, probe, swab, brush or high velocity air stream. During the removal process, the side walls of the coupling matrix may be inadvertently or purposefully concavely curved (e.g., filleted). The side walls of the digital representation of the coupling matrix may be curved to reflect any curvature that may occur during the flash removal process. Similarly, the side walls of the coupling matrix may be convexly curved (e.g., chamfered) to reflect curvature that might occur as a result of adhesive flashing out of the gap between the tooth and the appliance during appliance application.

Providing a digital representation of the coupling matrix may provide a useful and intuitive display with which practitioner 14 may interact to select a suitable orthodontic appliance for patient 16, adjust a characteristic of the orthodontic appliance (e.g., the torque, angulation, labial-lingual offset (in-out) and rotational offset of the appliance relative to the tooth) or otherwise visualize the fit between a particular orthodontic appliance and the surface of the patient's tooth. Because the surface features of a particular patient's tooth are typically unique to patient 16, it may be useful for practitioner 14 to determine how a particular orthodontic appliance fits relative to the tooth of the particular patient 16 within a virtual 3D environment prior to actually bonding the appliance to the tooth. Based on the configuration of the digital representation of the coupling matrix, practitioner 14 may determine whether the selected orthodontic appliance provides a satisfactory fit for the particular tooth of the particular patient. If practitioner 14 determines that a selected orthodontic appliance does not provide a satisfactory fit based on the digital representations of the coupling matrix, practitioner 14 may select another type of orthodontic appliance to model within the 3D environment provided by client computing device 12.

Although the description will generally discuss the display and positioning of one or more teeth and orthodontic brackets, it shall be understood that client computing device 12 may display and/or position any type of orthodontic appliance without departing from the scope of the present invention. Examples of such orthodontic appliances include, but are not limited to, orthodontic brackets, buccal tubes, sheaths or buttons. In addition, although a "custom base" is primarily referred to throughout the remainder of the disclosure, in other embodiments, computing device 12 may provide a digital representation and determine a thickness of any suitable coupling matrix for any suitable bonding technique, including, but not limited to, an adhesive pad in a direct bonding technique or a material that is integral with the orthodontic appliance and machined to define a base for the appliance.

In most cases, orthodontic brackets are configured to be applied to a particular tooth of the dental arch, such as a lower molar, but not to the individual tooth of a specific patient. The size, surface contour, and other characteristics of a particular tooth may differ between patients. Accordingly, a commercially available bracket (i.e., a bracket designed for use for multiple patients rather than customized for a particular patient) may interface with a particular patient's tooth in a different way than with another patient's tooth. In addition to connecting the custom base to the surface of the patient's tooth, the custom base fills the gaps between the bracket and the tooth. Because each patient's tooth typically has unique surface features, a thickness of the custom base and thickness distribution of the custom base may differ between patients. A "thickness" is generally measured substantially along the labial-lingual direction between the surface of the tooth and the respective surface of the bracket. The thickness of the custom base may also differ depending on what type of bracket practitioner 14 selects for use on the patient's tooth.

In addition to displaying a digital representation of the custom base that results from a particular bracket position, in some modes, client computing device 12 indicates a thickness of the custom base at one or more portions of the custom base and/or a volume of the custom base via an element within the 3D environment. The element may be, for example, a 3D object, text, graphics or geometric primitives (e.g., lines, curves, etc.) within the 3D environment that provides an indication of a thickness to practitioner 14. For example, in one embodiment, practitioner 14 may select one or more portions (e.g., clicking on the digital representation of the custom base with a peripheral pointing device, such as a mouse), and client computing device 12 may present a text box that provides a thickness of the custom base at the selected portion(s).

In another embodiment, client computing device 12 presents a thickness map of the custom base that indicates the different thicknesses of the custom base and variations in thickness. For example, client computing device 12 may present a thickness map that uses a color-coding scheme to distinguish between different thickness ranges. The color-coding scheme may be any suitable scheme including different colors, different shades of the same color or combinations of different colors and shades. As described in further detail below, each color and/or shade may indicate a gross thickness range or a thickness range relative to a predetermined baseline thickness. In some embodiments, the baseline thickness may be a norm thickness for practitioner 14, for multiple practitioners or may otherwise be selected by practitioner 14 or client computing device 12. In other embodiments, the baseline thickness may be a threshold thickness determined by client computing device 12, practitioner 14, the manufacturer of modeling software running on client computing device, or another suitable source. The threshold thickness may indicate the maximum and/or minimum acceptable thickness of the custom base for providing a sufficient bond strength. The thickness map may also be referred to as a "contour map" or a "topographic map" in embodiments in which the map is color-coded because the thickness map visually indicates the variation in the surface configuration of the surface of the custom base facing the tooth.

Practitioner 14 may use the digital representation of the custom base as a visual aid to determine whether a bracket position resulting from a particular treatment plan is suitable for patient 16, and if necessary, readjust a position of the bracket relative to the surface of the tooth within the 3D environment. For example, practitioner 14 may readjust the bracket position to minimize the thickness of the custom base at one or more points or to achieve a more uniform distribution of custom base. In embodiments in which client computing device 12 implements a bracket fitting algorithm in order to select a bracket and determine the bracket fit characteristics, practitioner 14 may visually confirm that the bracket fitting algorithm worked correctly based on the digital representation of the custom base.

The thickness distribution of the custom base may be indicative of the fit between the particular type of orthodontic appliance and the tooth of patient 16. In some cases, the practitioner may wish to achieve a uniform custom base thickness distribution in order to provide a more secure fit between the bracket and the tooth. In some cases, it may also be desirable to minimize the thickness of the custom base because a minimal thickness may substantially accurately reflect the in-out prescription of the appliance system. In addition, in some cases, minimizing the overall thickness of the custom base may result in a more reliable bond between the appliance and the tooth, compared to other, thicker custom bases. Some custom base distributions (or contours), such as a relatively uneven distribution on opposite sides of the custom base, may result in a weak bond between the tooth and the orthodontic appliance, and, in some cases, a bonding failure. In other cases, practitioner 14 may purposefully induce an uneven distribution of the custom base in order to achieve a particular result, such as a particular torque or direction of movement of the tooth.

Practitioner 14 may select the desired distribution of the custom base based on information such as the patient's case history, previous experience or the type of adhesive forming the custom base. The contour of the custom base may also be selected to orient the slot in the bracket for receiving an archwire in a desired direction. In some cases, it may be desirable for the archwire-receiving slot in the bracket to be oriented in a substantially horizontal direction, which is substantially parallel to the occlusal plane of the patient.

The custom base thickness and/or volume information may also provide a useful tool for determining the amount of adhesive or other bonding substance to dispense when applying the orthodontic appliance directly to the tooth of patient 16 in a direct bonding technique or to a physical model of the tooth in an indirect bonding technique. An accurate dispensing of adhesive may useful information in the case of a system in which a pick-and-place robot places brackets on a patient's teeth. Without the custom thickness and/or volume information, the practitioner may apply too much adhesive to the bracket and waste resources or the practitioner may apply an insufficient amount of adhesive to the bracket and potentially change the fit of the bracket to the tooth of the patient. An insufficient amount of adhesive may also result in gaps or voids between the bracket base and the tooth, which could weaken the resulting bond between the bracket and the tooth, result in bond failure, and/or serve as a trap for food and ultimately facilitate the formation of cavities.

In general, the digital representation of the custom base with a 3D environment may also help the practitioner determine whether the displayed bracket provides a satisfactory fit and whether another type of bracket would provide a better fit for the particular tooth of the patient. For example, if the custom base thickness exceeds a predetermined threshold at one or more portions, practitioner 14 may select another bracket or readjust a position of the bracket. The threshold may be determined by, for example, practitioner 14 or the manufacturer of the software running on client computing device 12. Furthermore, the threshold may be individualized to a particular patient or may be applicable to more than one patient. The thresholds may differ based on the tooth. For example, a greater range of thicknesses, i.e., a greater threshold, may be more tolerable for molars than for incisors.

Rather than directly manipulating the digital representation of the bracket in order to achieve a particular custom base thickness or thickness distribution, in some embodiments, modeling software 30 may present a GUI that enables practitioner 14 to specify the desired custom base thickness at one or more portions of the custom base. However, because only a certain custom base thickness may be achieved with a particular type of bracket, modeling software 30 may limit the available range of custom base thicknesses.

The thickness distribution of the custom base may be indicative of the balance of the bracket relative to the tooth. In many cases, a substantially evenly-distributed custom base may indicate a substantially balanced bracket because the distribution of the custom base is indicative of the spacing between the bracket and the tooth of the patient when the bracket is placed on the tooth. Accordingly, the thickness distribution of the custom base may indicate the extent of "rocking" that the bracket would be subjected to if the bracket was positioned on the tooth according to the bracket fitting algorithm. Practitioner 14 may control the balance of the bracket relative to a respective tooth of patient 16 by readjusting the bracket position until a desired custom base distribution is achieved.

Client computing device 12 may also display a digital representation of one or more orthodontic appliances associated with the teeth in addition to the digital representation of the custom base. In one embodiment, the orthodontic appliance is a bracket. However, in other embodiments, the orthodontic appliance may be any appliance that corresponds to a particular tooth of patient 16, or a particular set of teeth, where a set is generally less than a full dental arch of patient 16. Client computing device 12 need not display a full visual representation of an orthodontic appliance. Rather, a portion of the appliance may be displayed, such as an outline of the appliance or an outline of certain features of the appliance (such as features of the base of the appliance). In addition, client computing device 12 may display a full visual representation of an archwire or alternatively, a portion of an archwire, such as an outline of the archwire or an outline of certain features of the archwire.

The orthodontic appliance and/or archwire may be displayed as a visible object or partially visible object or alternatively, the appliance may be displayed as a substantially transparent object for clarity of illustration of the teeth and/or custom base. Displaying the appliance as a substantially transparent object or otherwise not displaying the appliance provides an interface in which a custom base is more visible than when the appliance is displayed as a substantially opaque object. While the custom base may still be visible when the appliance is displayed as a visible object, in some cases, it may be desirable to view the custom base without an overlying orthodontic appliance in order to better visualize the thickness map of the custom base.

As another alternative, client computing device 12 need not display the appliance itself. Rather, another object associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, indirect bonding trays, or other objects which may represent or be attached to an appliance, or which may be otherwise associated with an appliance and/or its placement. Alternatively, client computing device 12 may reference an orthodontic appliance analog (i.e., an orthodontic appliance represented by data, such as a coordinate system) instead of the device itself. The terms "appliance" or "bracket" as used herein shall therefore be understood to include any type of appliance, a full or partial representation of an appliance, any object associated with an appliance and/or its placement or an analog of the orthodontic appliance.

As described in detail herein, client computing device 12 presents a graphical user interface (GUI) with which practitioner 14 interacts to define a prescription for patient 16. Practitioner 14 may interact with the GUI presented by client computing device 12 to view the digital representation of the teeth within the 3D environment, define a proposed orthodontic prescription, and determine the proper placement of one or more brackets with respect to one or more teeth for achieving a desired functional and/or aesthetic result. That is, practitioner 14 selects virtual brackets and directly manipulates the virtual brackets within the 3D environment to position the brackets on individual teeth within the modeled dental arch. To aid the practitioner, client computing device 12 may initially place the virtual brackets on individual teeth based on standard prescriptions for commercially available brackets, an initial prescription specified by practitioner 14, or via a bracket fitting algorithm.

Examples of bracket fitting algorithms or techniques that client computing device 12 may implement to initially place brackets within the 3D environment are described in commonly assigned U.S. Pat. No. 7,210,929, entitled "Method of Placing Orthodontic Brackets on Teeth in a 3D Virtual World," which issued May 1, 2007, and commonly assigned U.S. Patent Application Publication No. 2006/0024637, entitled "Automatic Adjustment of an Orthodontic Bracket to a Desired Occlusal Height Within a Three-Dimensional (3D) Environment," filed Jul. 30, 2004 by Raby, et al., both of which are incorporated herein by reference in their entireties. A system for placing teeth and/or brackets along an archwire is described in commonly assigned U.S. Patent Application Publication No. 2006/0073436, entitled "Movement of Orthodontic Objects Along a Archwire Within a Three-Dimensional (3D) Environment" filed Apr. 6, 2006 by Raby, et al., which is incorporated herein by reference in its entirety.

In some cases, client computing device 12 also presents an environment in which practitioner 14 may manually place orthodontic brackets relative to teeth within the 3D environment. Manual placement of the brackets may be assisted by use of visual planar guides, as described in commonly assigned U.S. Patent Application Publication No. 2005/0170309, entitled "Planar Guides to Visually Aid Orthodontic Appliance Placement within a Three-Dimensional (3D) Environment", filed Feb. 4, 2004 by Raby, et al., which is incorporated herein by reference in its entirety.

It shall be understood that these and/or any other techniques may be used to initially place the brackets on the teeth in the 3D environment and thus determine the patient's prescription, and that the invention is not limited in this respect. Moreover, although described for purposes of illustration with respect to modeling software executing on client computing device 12, the techniques may be applied by any computing device, including servers remote from practitioner 14.

Client computing device 12 may then compute the resulting final position of the modeled teeth resulting from the initial bracket placement. Practitioner 14 may subsequently adjust the position of a particular bracket relative to a particular tooth to achieve a desired functional and/or aesthetic result. Practitioner 14 may adjust the position of a particular bracket based on the digital representation of the custom base, because, as previously discussed, the thickness and thickness distribution of the custom base may indicate the balance of the bracket relative to a particular tooth. For example, practitioner 14 may manually adjust the position of the bracket, such as by selecting the bracket with a mouse or another peripheral pointing device and manipulating the bracket within the 3D environment. Practitioner 14 may, for example, drag the bracket to a desired position within the 3D environment or reorient the bracket. Alternatively, practitioner 14 may select a bracket and reposition the bracket within the 3D environment by manually inputting coordinates for the bracket. Practitioner 14 may also activate a refit algorithm implemented by client computing device 12 in order to automatically reposition the bracket within the 3D environment. In other embodiments, practitioner 14 may implement any suitable technique for repositioning a bracket within the 3D environment. In some embodiments, client computing device 12 may then recompute the placement of the modeled teeth resulting from the manipulation of the brackets by practitioner 14. Furthermore, after each bracket positioning iteration, client computing device 12 may regenerate the custom base that results from the respective bracket position.

Once a proposed orthodontic prescription is formulated and displayed, the brackets are placed to achieve a final functional and/or aesthetic result, and/or such other result as may be desired, and practitioner 14 has indicated his or her approval, client computing device 12 communicates the bracket placement positions to manufacturing facility 18 via network 20. In response, manufacturing facility 18 constructs an indirect bonding tray 22 for use in physically placing brackets on the teeth of patient 16. In other words, manufacturing facility 18 fabricates indirect bonding tray 22 based on the bracket placement positions selected by practitioner 14 within the 3D environment presented by client computing device 12. Manufacturing facility 18 may, for example, use conventional commercially available brackets selected by practitioner 14 to form indirect bonding tray 22. Manufacturing facility 18 forwards indirect bonding tray 22 to practitioner 14 for use in a conventional indirect bonding procedure to place the brackets on the teeth of patient 16. As another option, manufacturing facility 18 constructs, instead of the indirect bonding tray 22, a custom jig for placing a single bracket on the patient's tooth or a group of brackets on, e.g., a quadrant of a dental arch or an entire dental arch.

Alternatively, client computing device 12 need not forward the bracket placement positions to manufacturing facility 18. Client computing device 12 may instead output, e.g., display or print, the relevant distances and angles for each bracket to assist practitioner 14 in manually positioning the brackets on the teeth of patient 16 in a direct bonding technique. Alternatively, client computing device 12 may print a 2D representation of the 3D images displayed on the graphical user interface of client computing device 12.

Figure 2:
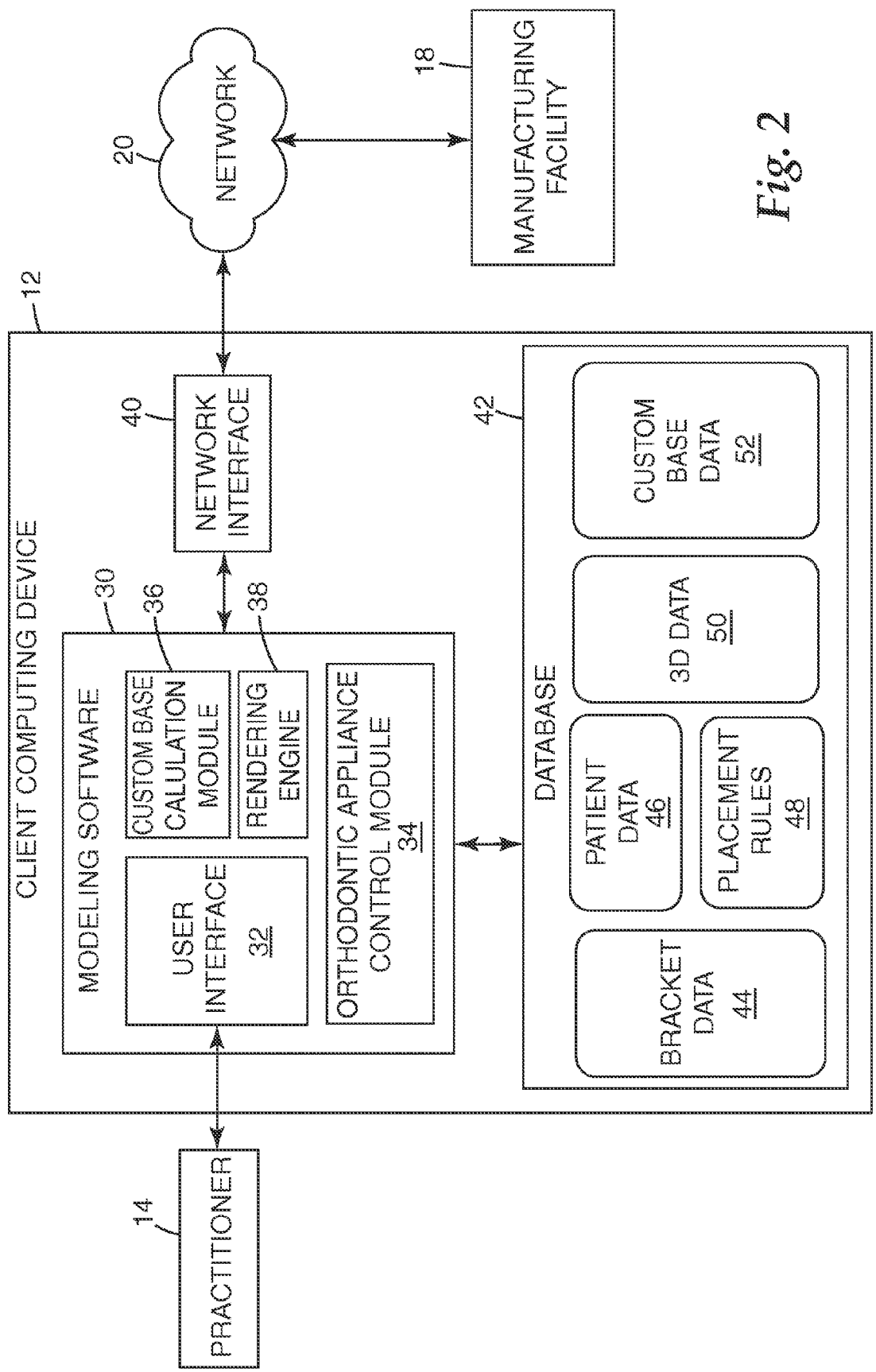
FIG. 2 is a block diagram illustrating an example embodiment of the client computing device of FIG. 1 in further detail.

FIG. 2 is a block diagram illustrating an example embodiment of client computing device 12 in further detail. In the illustrated embodiment, client computing device 12 provides an operating environment for modeling software 30. As described above, modeling software 30 presents a modeling environment for modeling and depicting the digital representation of the teeth of patient 16 (FIG. 1), as well as the digital representations of one or more orthodontic appliances and coupling matrices formed between the orthodontic appliance and a respective tooth. In the illustrated embodiment, modeling software 30 includes a user interface 32, orthodontic appliance control module 34, custom base calculation module 36, and rendering engine 38. Modeling software 30 interfaces with network 20 via network interface 40. Although referred to as a "custom base" calculation module 36, in other embodiments, calculation module 36 may generally be a "coupling matrix" calculation module that calculates a thickness, volume or other geometry and dimensions of any suitable type of coupling matrix, e.g., an adhesive pad for a direct bonding technique.

User interface 32 provides a GUI that visually displays the digital representation of the patient's dental arch and/or of specified portions of the patient's dental arch as well as digital representations of the brackets (or other orthodontic appliance) and custom bases of the brackets for connecting to the patient's teeth. The digital representations may be 3D or two-dimensional (2D). In addition, user interface 32 provides an interface for receiving input from a user, such as practitioner 14, e.g., via a keyboard and a peripheral device, for manipulating a tooth or bracket.

Orthodontic appliance control module 34 and custom base calculation module 36 may be considered interactive modules for developing an orthodontic treatment plan for achieving a desired tooth arrangement for a particular patient 16 (FIG. 1). In some embodiments, practitioner 14 may interact with modeling software 30 via user interface 32 to indicate a desired position of a bracket associated with the particular tooth. Orthodontic control module 34 may also move the bracket based on the movement inputted by practitioner 14. In embodiments in which a digital representation of the bracket is rendered and displayed on user interface 32, the adjusted position of the bracket may be displayed via the GUI of user interface 32. Practitioner 14 may interact with custom base calculation module 36 in order to determine a custom base thickness or volume. For example, practitioner 14 may select a portion of the representation of the custom base for which more information is desired, and in response, custom base calculation module 36 may provide practitioner 14 with details about the selected custom base portion. As another example, custom base calculation module 36 may provide practitioner 14 with a custom base thickness map.

As described above, during treatment, commercially-available brackets are configured to be placed on a particular tooth (e.g., a lower molar), but not to the individual tooth of a particular patient, which may have unique surface features. Accordingly, an adhesive may not only bond the bracket to the surface of the tooth, but may also fill any gaps between the tooth and the bracket, thereby creating a customized structure for applying the bracket to the tooth of the patient. In an indirect bonding technique, the custom base is created during a preliminary stage when the brackets are attached to a physical model of a patient's teeth. Another adhesive is used to bond the custom base to the patient's actual teeth during the bonding stage.

Many existing systems that provide digital representations of orthodontic appliances and teeth for the purposes of generating an orthodontic treatment plan illustrate the bracket "floating" in free space relative to the tooth. The floating bracket may make it difficult for practitioner 14 to visually ascertain how well a bracket base conforms to a tooth as placed in the 3D environment. For example, the gap between the bracket and the tooth may make it difficult to judge the thickness of the custom base when only the gap is shown, particularly because the gap is not fully illustrated and merely the outer boundaries of the gap are shown. On the other hand, rendering engine 38 renders a digital representation of the custom base in order to help practitioner 14 visually ascertain the bracket fit. The digital representation of the custom base may include both the side walls (or outer boundaries) of the custom base, which include the surfaces extending between the tooth and the bracket, and the inner surface, which includes the surface of the custom base that substantially faces the orthodontic appliance or the tooth. It may be desirable to view the inner surface of the custom base in addition to the outer boundaries because the inner surface may vary considerably in contour, depending on the patient's tooth surface characteristics. Custom base calculation module 36 determines different characteristics of the custom base, such as the thickness at one or more portions of the custom base or the volume of the custom base, to further aid the treatment planning for a particular patient 16.

Custom base calculation module 36 may render at least one element within the 3D environment that visually represents the thickness of at least a portion of the custom base. The element may be, for example, a 3D object, text, graphics or geometric primitives (e.g., lines, curves, etc.) within the 3D environment that provides an indication of a thickness to practitioner 14. For example, in one embodiment, custom base calculation module 36 may indicate a thickness at one or more custom base portions by generating a thickness map that rendering engine 38 presents to practitioner 14. The thickness map visually indicates the thicknesses of different portions of the custom base. The thickness map may be interactive. Practitioner 14 may select one or more portions of the thickness map in order to obtain further details about the thickness at the selected portions.

In some embodiments, custom base calculation module 36 generates a color-coded thickness map, in which different colors or shades of one or more colors represent different custom base thicknesses (measured in a substantially labial-lingual direction). While a digital representation of a custom base having a uniform color may be useful, color-coding the digital representation of the custom base may add additional utility to the display of the custom base. For example, the color-coded thickness map of the custom base may enable practitioner 14 to quickly distinguish between different thicknesses. A black-and-white thickness map may also be useful in certain instances. For example, shades of gray, or different types of cross-hatching or other graphical indicia, may be used to indicate different thicknesses.

Different color coding schemes may be used. For example, in one embodiment, different colors may represent different ranges of absolute custom base thicknesses. Each color may represent any suitable thickness range. For example, each color may represent a thickness range of about 0.05 mm to about 0.5 mm. Any number of colors may also be used. In one embodiment, custom base calculation module 36 implements a color-code scheme that includes three to seven colors representing three to seven thickness ranges. For example, custom base calculation module 36 may generate a thickness map that includes about five thickness ranges. Colors or different shades of one or more colors that are readily distinguishable from each other may be used in order to provide a display that practitioner 14 may quickly review and quickly ascertain the variation in thickness, and, in some cases, the thickness of different portions of the custom base. For example, blue may indicate a thickness range of about 0 mm to about 0.12 mm, green may indicate a thickness range of about 0.13 mm to about 0.25 mm, yellow may indicate a thickness range of about 0.26 mm to about 0.38 mm, orange may indicate a thickness range of about 0.39 mm to about 0.50 mm, and red may indicate a thickness greater than 0.51 mm. Other color coding schemes and thickness ranges may be used. The color may change discretely as the thickness changes, or the color may continuously change to more accurately depict the contour of the custom base.

In another embodiment, different colors may represent the deviation from a baseline thickness, such as a norm thickness or thickness threshold, where the baseline thickness may be selected by a practitioner, by a manufacturer of modeling software 30 or by modeling software 30. For example, modeling software 30 may "learn" a norm thickness based on past usage by a certain practitioner 14. That is, modeling software 30 may learn that practitioner 14 prefers a custom base thickness in a certain range, such as after repetitive adoption of a custom base thickness or an average custom base thickness. Alternatively, the norm may be based on the practice of more than one practitioner. The norm thickness may be represented as a first color and other colors may be used to indicate different thickness ranges relative to the norm. In another embodiment, the norm thickness may be a norm thickness associated with at least one set of orthodontic appliances, such as a certain type of bracket. Modeling software 30 may learn the norm thickness for a particular type of orthodontic appliance based on past usage by a one or more practitioners 14, or the appliance manufacturer may specify a norm thickness. Again, the colors that indicate a deviation from a norm thickness may represent any suitable number of thickness ranges, such as about three to about seven thickness ranges.

In embodiments in which different colors represent the deviation from a threshold thickness value, custom base control module 36 may generate a custom base in a uniform color and use one or more colors to indicate the range of thicknesses by which the custom base exceeds the threshold value. Custom base control module 36 may also generate an indication to inform practitioner 14 that the thickness of the custom base exceeds the threshold value at one or more points, and may specify the regions via the color-coded thickness map.

In other embodiments, rendering engine 38 may render a custom base having a uniform color and custom base calculation module 36 may provide an interactive feature by which practitioner 14 may select one or more portions of the custom base in order to obtain more information about the thickness at the selected portions. For example, practitioner 14 may select a portion of the displayed custom base with a mouse or another peripheral pointing device, and custom base calculation module 36 may render at least one element that includes text, such as within a GUI display area, where the text includes detailed information about the selected portion of the custom base, such as the thickness of the custom base at the selected portion.

In other embodiments, rendering engine 38 may indicate a thickness distribution of the custom base via a contour map. Contour lines may be drawn on the digital representation of the custom base, the surface of the respective tooth or the base of the orthodontic appliance. Each contour line may follow a path of constant thickness, and the thickness value associated with each contour may be illustrated, for example, by a numerical value shown in close proximity to the line, in a separate GUI window or textbox that appears when practitioner 14 positions a cursor over the contour line or by color-coding the line according to a legend that maps colors (or monochrome values) to thicknesses.

If practitioner 14 adjusts a position of a bracket relative to a tooth of patient 16, modeling software 30, and in particular, custom base control module 36 may recalculate the thickness of the custom base and rendering engine 38 may render a thickness map reflecting the thickness of the custom base or otherwise indicate a thickness of the custom base. Any of the aforementioned techniques for indicating a thickness of one or more portions of the custom base calculation module may be combined, and in other embodiments, custom base calculation module 36 may implement other techniques for indicating a thickness of a custom base.

As previously discussed, practitioner 14 may readjust a position of a bracket via user interface 32 in order to achieve a desired custom base distribution or a desired tooth position or dental arch arrangement for patient 16. Modeling software 30 may receive an input indicative of a desired position for a bracket in multiple different ways. For example, modeling software 30 may implement a technique described in commonly-assigned U.S. patent application Ser. No. 11/551,372, entitled, "DIGITAL ORTHODONTIC TREATMENT PLANNING," and filed on Oct. 20, 2006, the entire content of which is incorporated herein by reference. U.S. patent application Ser. No. 11/551,372 describes a technique by which practitioner 14 may interact with modeling software of a computing system in order to visualize the 3D representation of the dental arch, indicate a desired position or desired movement for one or more teeth, and determine a position of one or more orthodontic appliances that will result in the desired tooth position. In U.S. patent application Ser. No. 11/551,372, the system implements certain techniques that provide the practitioner with the perception that he or she is directly manipulating the 3D representation of the patient's teeth so as to specify final (i.e., desired) tooth positions. However, in response to input from the practitioner, the computing system computes an adjustment to a current position of a bracket (or another orthodontic appliance). That is, instead of directly manipulating a tooth within the 3D environment (as the practitioner perceives) the movements input by the practitioner are instead applied to the appliance associated with the tooth, but in a reverse fashion. The system then computes a new position for the tooth based on the adjustment to the appliance.

If practitioner 14 indicates a desired bracket or tooth position to balance or minimize the thickness of the virtual custom base by manipulating a bracket, orthodontic appliance control module 34 may refit the digital representation of the tooth relative to the indicated bracket position (either continuously or incrementally as mouse, button or other input events are received) in response to the input from practitioner 14 indicating the desired bracket position. In another embodiment, which may be another mode of operation of modeling software 30, practitioner 14 may be given more direct control of tooth movements that result in tooth positions. An ability to directly manipulate tooth positions may enable practitioner 14 to effectively achieve intermediate tooth positions to those offered by a best-fit configuration of the bracket relative to the tooth. Best-fit configurations typically rely on discrete metrics (e.g., torque, angulation, in/out) for the bracket position. A wider range of final tooth positions may be achieved by allowing imbalances in the thickness distribution of the custom base. Such imbalances are more easily visualized by using a custom base thickness map. In addition, the custom base thickness map may also enable practitioner 14 to maintain the imbalance within acceptable limits.

In some embodiments, user interface 32 may include navigational controls for moving and/or positioning the orthodontic object, such as by clicking on an icon that displays navigational controls for moving a virtual tooth and/or bracket. The result is that modeling software 30 allows practitioner 14 to interactively create a treatment plan for a patient by generating an initial bracket placement for a tooth, predicting the resulting position of the tooth based on the initial bracket placement, and enabling practitioner 14 to adjust the position of the bracket or select another type of bracket using the digital representation of a custom base as a tool to visualize the fit between the bracket and a respective tooth. The digital representation of the custom base provided by rendering engine 38 and the thickness map provided by custom base control module 36 enables practitioner 14 to reposition a bracket and/or tooth with more precision and accuracy by providing additional information that may be useful in determining whether repositioning of a bracket is desirable.

Modeling software 30 interacts with database 42 to access a variety of data, such as bracket data 44 (including data regarding the bracket base), patient data 46, placement rules 48, 3D data 50, and custom base data 52. Although referred to as "custom base" data 52, in other embodiments, database 42 may include data 52 for other types of coupling matrices. Database 42 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS), object relational (ORDBMS) or other type of database management system. The data may, for example, be stored within a single relational database such as SQL Server from Microsoft Corporation. Although illustrated as local to client computing device 12, database 42 may be located remote from client computing device 12 and coupled to client computing device 12 via a public or private network, e.g., network 20.

Bracket data 44 describes a set of commercially available brackets or other orthodontic appliances that may be selected by practitioner 14 and positioned within the 3D modeling environment. For example, bracket data 44 may store a variety of attributes for the commercially available brackets, such as dimensions, slot locations and characteristics, torque angles, angulations and other attributes. User interface 32 may provide a menu-driven interface by which practitioner 14 selects the type of brackets for use in defining an orthodontic prescription for patient 16 (FIG. 1). Bracket data 44 may also include bracket-tooth behavior rules that define a relationship between each bracket and respective tooth.

Patient data 46 describes a set of one or more patients, e.g., patient 16 (FIG. 1), associated with practitioner 14. For example, patient data 46 specifies general information, such as a name, birth date, and a dental history, for each patient. Optionally, patient data 46 includes appointment scheduling information and billing information. In addition, patient data 46 specifies a current prescription specified for each of the patients, including the types of brackets selected by practitioner 14 for use with each of the patients, and their associated positions and orientations on the teeth of patient 14. Patient data 46 may also include information regarding the composition, structure or construction of selected bracket base. After practitioner 14 determines a desirable bracket placement position via modeling software 30, practitioner 14 may store the bracket placement position within patient data 46 of database 42.

Placement rules 48 may specify industry-defined placement rules for commercially available orthodontic appliances. In addition, placement rules 48 may include user-defined rules specified by practitioner 14 or other rules for controlling appliance placement. Modeling software 30 and/or practitioner 14 (or a technician under the direction of practitioner 14) may reference placement rules 48 to initially place brackets or other orthodontic appliances with respect to one or more teeth of a patient prior to arranging teeth into a desired arch form.

One rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a custom base of the bracket on the FACC of the tooth equidistant from the occlusal edge or occlusal-most point on the FACC and the gingival margin of the crown. This location is also known as the Facial Axis Point (FA Point). As another example, practitioner 14 may desire to place brackets at a position that is different from the FA Point. Consequently, practitioner 14 may specify different prescriptions for different types of teeth in the dentition, for different types of brackets, or both. Optionally, the prescription may be based in whole or in part on known rules associated with a particular type of the appliances selected by practitioner 14.

Placement rules 48 may also include bracket fitting algorithms or other techniques for placing brackets within the 3D environment. The stored algorithms may include U.S. Pat. No. 7,210,929, entitled "Method of Placing Orthodontic Brackets on Teeth in a 3D Virtual World," which issued May 1, 2007, U.S. Patent Application Publication No. 2005/0170309, entitled "Planar Guides to Visually Aid Orthodontic Appliance Placement within a Three-Dimensional (3D) Environment", filed Feb. 4, 2004 to Raby, et al., U.S. Patent Application Publication No. 2006/0024637, entitled "Automatic Adjustment of an Orthodontic Bracket to a Desired Occlusal Height Within a Three-Dimensional (3D) Environment", filed Jul. 30, 2004 by Raby, et al., and U.S. Patent Application Publication No. 2006/0073436, entitled "Movement of Orthodontic Objects Along a Virtual Archwire within a Three-Dimensional (3D) Environment" filed Apr. 6, 2006 by Raby, et al., which were previously incorporated by reference.

Rendering engine 38 accesses and renders 3D data 50 to generate the 3D view presented to practitioner 14 by user interface 32. More specifically, 3D data 50 includes information defining the 3D objects that represent each tooth, orthodontic appliance, and custom base within the 3D environment. Rendering engine 38 processes each object to render a 3D triangular mesh based on viewing perspective of practitioner 14 within the 3D environment. User interface 32 displays the rendered 3D triangular mesh to practitioner 14, and allows practitioner 14 to change viewing perspectives and manipulate objects within the 3D environment. If rendering engine 38 renders brackets, or any other orthodontic appliances, as transparent or visible objects, rendering engine 38 may initially place the brackets in the 3D environment using any of several different techniques described above.

Custom base data 52 stores information relating to different types of custom bases, such as different types of adhesives that practitioner 14 may use to create the custom bases. Custom base data 52 may also store the baseline (e.g., a norm or threshold) custom base thicknesses for one or more teeth, where the baseline thickness may be specific to a particular practitioner 14, clinic (i.e., multiple practitioners) or orthodontic appliance. Custom base calculation module 36 may reference the baseline thickness when creating a thickness map of the custom base.

Figure 3:
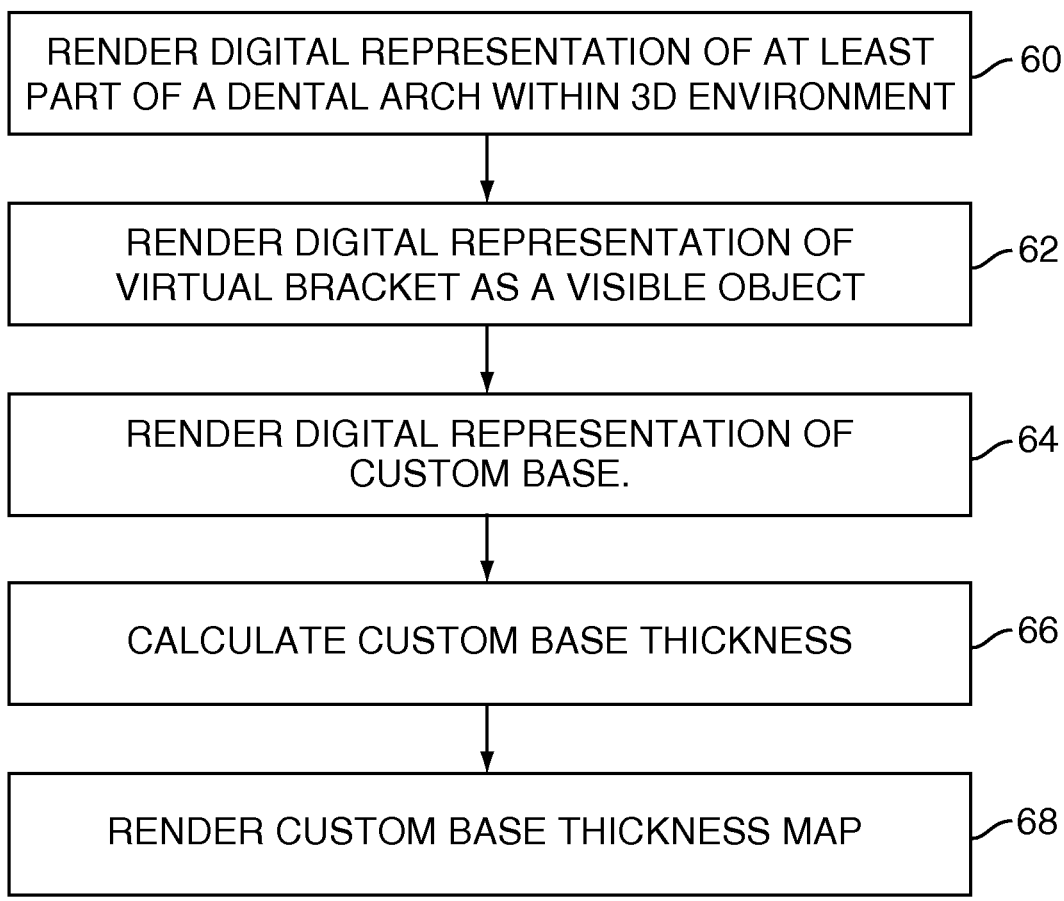
FIG. 3 is a flow diagram illustrating a process for displaying a coupling matrix thickness map within a three-dimensional (3D) environment that includes a digital representation of the coupling matrix and of at least one tooth.

FIG. 3 is a flow diagram illustrating a process for displaying a custom base thickness map within a 3D environment presented by modeling software 30 of computing device 12 (FIG. 2). Rendering engine 38 of modeling software 30 renders a digital representation of at least a part of a dental arch of a patient within a 3D modeling environment (60). Rendering engine 38 may render one tooth, multiple teeth or the entire dental arch. In some embodiments, rendering engine 38 also renders a digital representation of a bracket (or another orthodontic appliance) as a visible object (62). However, as described above, in other embodiments, rendering engine 38 may render a bracket as a substantially transparent object. Orthodontic appliance control module 34 of modeling software 30 may implement a fitting algorithm to determine an initial position of the digital representation of the bracket relative to the digital representation of the respective tooth of the dental arch within the 3D environment.

Rendering engine 38 renders a digital representation of a custom base (64). As described in further detail below, custom base calculation module 36 of modeling software 30 may determine the configuration of the custom base based on the relative distance between the tooth and the bracket within the 3D environment. Even in embodiments in which the bracket is rendered as a transparent object or not rendered at all, orthodontic appliance control module 34 determines an initial position of the bracket within the 3D environment relative to the tooth. Custom base calculation module 36 may utilize this information to determine the configuration of the custom base that rendering engine 38 (64) presents to practitioner 14 via user interface 32, as well as to calculate a custom base thickness (66). In some embodiments, custom base calculation module 36 generates a custom base thickness map (68) for rendering by rendering engine 38. As previously described, the custom base thickness map is similar to a contour map and may include different colors or shading to distinguish between different thicknesses of the custom base.

Custom base calculation module 36 may determine a custom base thickness to generate the thickness map (68) by calculating the relative distance between the virtual bracket and the facial surface of the tooth at multiple points, such as based on the coordinates of the surface of the virtual bracket facing the tooth and the facial surface of the tooth within the 3D environment presented by modeling software 30. In some embodiments, custom base calculation module 36 may then interpolate between the calculated thicknesses in order to create a substantially continuous thickness map. In other embodiments, custom base calculation module 36 may present a thickness map including the thicknesses of discrete points of the map. The colors of each discrete point may be blended together to represent a gradually changing thickness.

In embodiments in which the virtual bracket is rendered as a visible object (60), the digital representation of the custom base is disposed between the bracket and the tooth within the 3D environment. In embodiments in which the virtual bracket is rendered as a substantially transparent object (or not rendered), the top surface of the custom base, i.e., the surface facing the bracket, may be more clearly illustrated. The custom base thickness map is more clearly shown when the virtual bracket is rendered as a substantially transparent object.

Figure 4A:
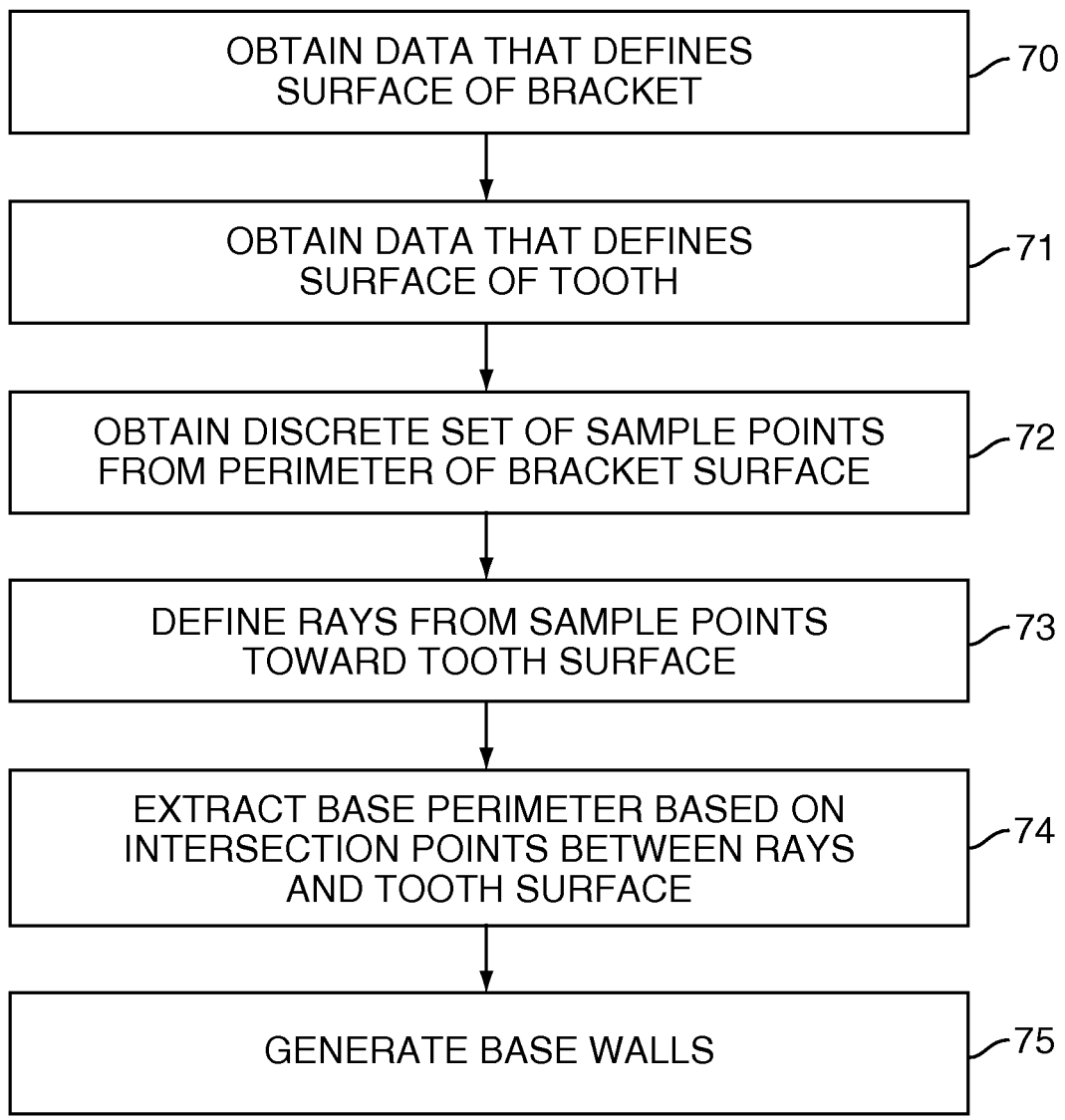
FIG. 4A is a flow diagram illustrating one technique for generating a digital representation of a coupling matrix within a 3D environment.

FIG. 4A is a flow diagram illustrating one technique for generating a digital representation of a custom base within a 3D environment. As previously described, in one embodiment, the digital representations of a patient's dental arch and orthodontic appliances are displayed via a 3D triangular mesh. After orthodontic appliance control module 34 (FIG. 2) implements a best-fit algorithm to place a virtual bracket within the 3D environment relative to a tooth or teeth to which the appliance is to be attached, rendering engine 38 obtains data that defines the surface of the virtual bracket facing the tooth (70) and data that defines a surface of the tooth to which the bracket is to be applied (71). The 3D data may be stored within 3D data 50 of database 42 (FIG. 2) of client computing device 12.

Rendering engine 38 may select discrete sets of sample points within the 3D environment from the data defining the outer perimeter of the bracket surface (72). For example, in embodiments in which the digital representation of the bracket is displayed via a triangular mesh, the sample points may be the outermost vertices of the triangles along the perimeter of the surface of the virtual bracket facing the tooth. A sufficient number and distribution of sample points to at least roughly characterize the configuration and size (i.e., length and width) of the outer perimeter of the bracket surface should be selected. For example, at least three, but up to fifty or more sample points may be used.

Rendering engine 38 may then define a plurality of hypothetical reference lines or rays, where at least one ray extends from each of the sample points toward the triangular mesh defining the digital representation of a respective tooth of the dental arch (73). Each ray is a substantially straight line emanating from a point, and the rays extend substantially parallel to each other. In one embodiment, the rays extend from the outermost vertices of the triangles along the perimeter of the surface of the virtual orthodontic appliance facing the tooth toward the triangular mesh defining the tooth along a lingual-labial reference axis. The triangular mesh defining the surface of the virtual bracket that faces the tooth also defines a surface of the virtual custom base because the custom base abuts the orthodontic appliance and substantially molds thereto.

The hypothetical rays are referenced herein in order to aid in describing an example of a technique employed by rendering engine 38 (FIG. 2) to render a digital representation of a custom base. The virtual bracket may be displayed as a substantially transparent object, visible object, or otherwise. In embodiments in which the virtual bracket is not displayed, orthodontic appliance control module 34 (FIG. 2) may provide custom base calculation module 36 with the location of the orthodontic appliance, such as by providing custom base calculation module 36 with coordinates of the surface of the orthodontic appliance closest to the respective tooth.

An outer perimeter of the custom base is extracted by connecting the points of intersection between the rays and the triangular mesh defining the tooth (74). The points of intersection define a polyline, which represents a perimeter of the custom base. The ray-triangle intersection points may be ordered similarly to the points on the virtual orthodontic appliance perimeter from which they originate. As one example, a Mobile 3D Graphics API application running on client computing device 12 (FIG. 2) may implement pick methods to extract the points of intersection between rays and the triangular mesh defining the tooth. Mobile 3D Graphics API is a specification defining an application programming interface for Java-based programs that produce computer graphics.

Sample points may also be collected at points other than the outer perimeter of the bracket surface. Rays may be projected from these sample points in order to calculate a thickness of the custom base at the respective sample point. That is, the length of the ray extending between the bracket surface and the tooth surface substantially equals a thickness of the custom base at the ray's sample point of origin. Custom base calculation module 36 may implement any suitable mathematical function in order to determine the length of each of the rays, such as by calculating the difference in coordinates of the origin of the ray at the bracket surface and the end of the ray at the tooth surface.

The walls of the custom base may be generated by enclosing the space between the rays extending between the triangular mesh defining the orthodontic appliance and the triangular mesh defining the tooth because the rays essentially define the outer surface of the custom base (75). Triangles may be formed in the enclosed space to define a closed or solid 3D object. For example, edges of each triangle are formed by pairing each originating point in the perimeter with its corresponding ray-triangle intersection point on the tooth. Edges are also formed by pairing each originating point in the perimeter with its neighbor's corresponding ray-triangle intersection point on the tooth. "Neighbors" for each point are always in the same direction (e.g., clockwise or counterclockwise). Together, the ray-triangle intersections on the tooth form another 3D polyline that is used to define a subset of the triangles on the facial surface of the tooth. The resulting 3D polyline may be used to cut, extract, or otherwise form a copy of the triangles on the tooth and use them to define a surface of the virtual custom base. In this way, enclosing the space between adjacent rays defines a substantially smooth outer surface of a custom base and a 3D shape of the custom base. In some embodiments, the volume of the virtual custom base is not converted to a closed or solid 3D object.

The total volume of the virtual custom base may be calculated using any suitable volume-computing algorithm. As previously indicated, the total volume of the virtual custom base indicates the volume of the custom bonding base plus the volume of any adhesive or other bonding material to be used to bond, affix or otherwise attach the appliance to the tooth of the patient. The volume of adhesive may also be combined for each tooth in the dental arch, thereby indicating how much adhesive is expected to be consumed in the bonding process for the patient, rather than the volume per tooth. Practitioner 14 may utilize the volume information to manage supplies, such as to preorder a sufficient amount of adhesive for a certain time period, such as a week, a month or otherwise. The total volume may also indicate how well the orthodontic appliance conforms to the surface of the tooth of the patient. A large custom base volume may indicate that the bracket does not conform well to the tooth of patient 16.

In some embodiments, custom base calculation module 36 may determine a volume of the virtual custom base by subdividing the volume into a plurality of columns extending lengthwise in a substantially labial-lingual direction. For example, a plurality of triangular columns may be generated by projecting rays from a vertex of each triangular mesh base of the custom base (or the surface of the orthodontic appliance facing the custom base which defines a "cap" of the custom base) toward the tooth. As another example, a plurality of triangular columns may be generated by projecting rays from a center of each triangle of the triangular mesh base of the custom base (or the surface of the orthodontic appliance facing the custom base) toward the tooth. The cross-sectional area of each column may be substantially equal to a cross-sectional area of a corresponding triangle of the custom base, by triangles on both ends of the column or by a regular rectangular grid or another pattern. Thus, in some embodiments, each column has substantially the same cross-sectional area, but differing lengths. In other embodiments, the columns have substantially different cross-sectional areas. The length of each column is measured in substantially the same direction as a thickness (i.e., the labial-lingual direction).

Each column may be colored according to its length, which is measured along the labial-lingual direction, its volume, or a deviation of the length or volume from a baseline length or volume. As previously described, a baseline length or any baseline value may be a norm value or threshold value selected by practitioner 14, modeling software 30, the manufacturer of modeling software 30 or another source. The baseline may be practitioner specific or applicable to more than one practitioner. In embodiments in which the columns each have substantially the same cross-sectional area, the colors of the color-coding system also represent the different volumes of each column. A color-coded thickness may be generated via the color-coded columns, where the entire map is visible from a labial perspective when the bracket is not displayed as a visible object and partially visible from the occlusal, gingival, mesial, and distal directions. The colors of each column may be blended together to represent a gradually changing thickness.

Figure 4B:
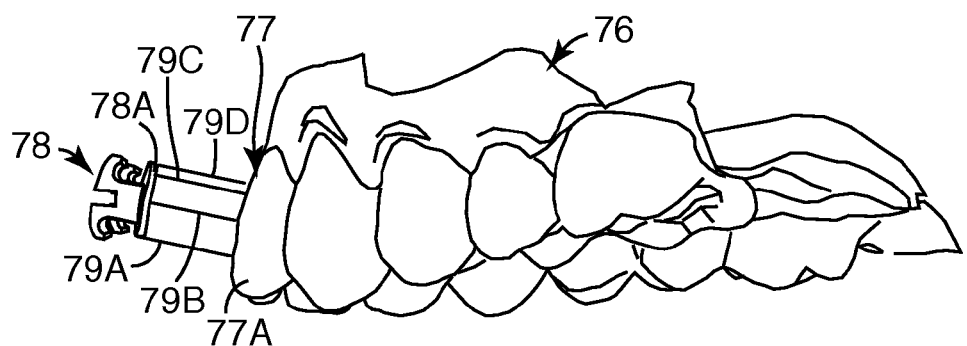
FIG. 4B is a schematic diagram including a digital representation of a dental arch and bracket 78 within a 3D environment, and illustrates hypothetical rays projecting from the bracket toward the tooth to define a coupling matrix.

FIG. 4B is a schematic diagram illustrating a digital representation of dental arch 76 including a tooth 77 and a digital representation of bracket 78 within a 3D environment. Bracket 78 is aligned to be applied to labial surface 77A of tooth 77. FIG. 4B illustrates an example of hypothetical rays 79A-D that may be used to generate a digital representation of a custom base. Rays 79A-D project from surface 78A of bracket facing tooth 77 toward labial surface 77A of tooth 77. In particular, rays 79A-D extend from a sample point on an outer perimeter of surface 78A of bracket 78 toward labial surface 77A of tooth 77A. Rays 79A-D are substantially parallel to each other and are spaced around the outer perimeter of surface 78A of bracket 78 in order to help define the outer boundaries of the custom base. Although four hypothetical lines are shown in FIG. 4B, in other embodiments, any suitable number of hypothetical rays may be used to generate a digital representation of a custom base.

Figure 5:
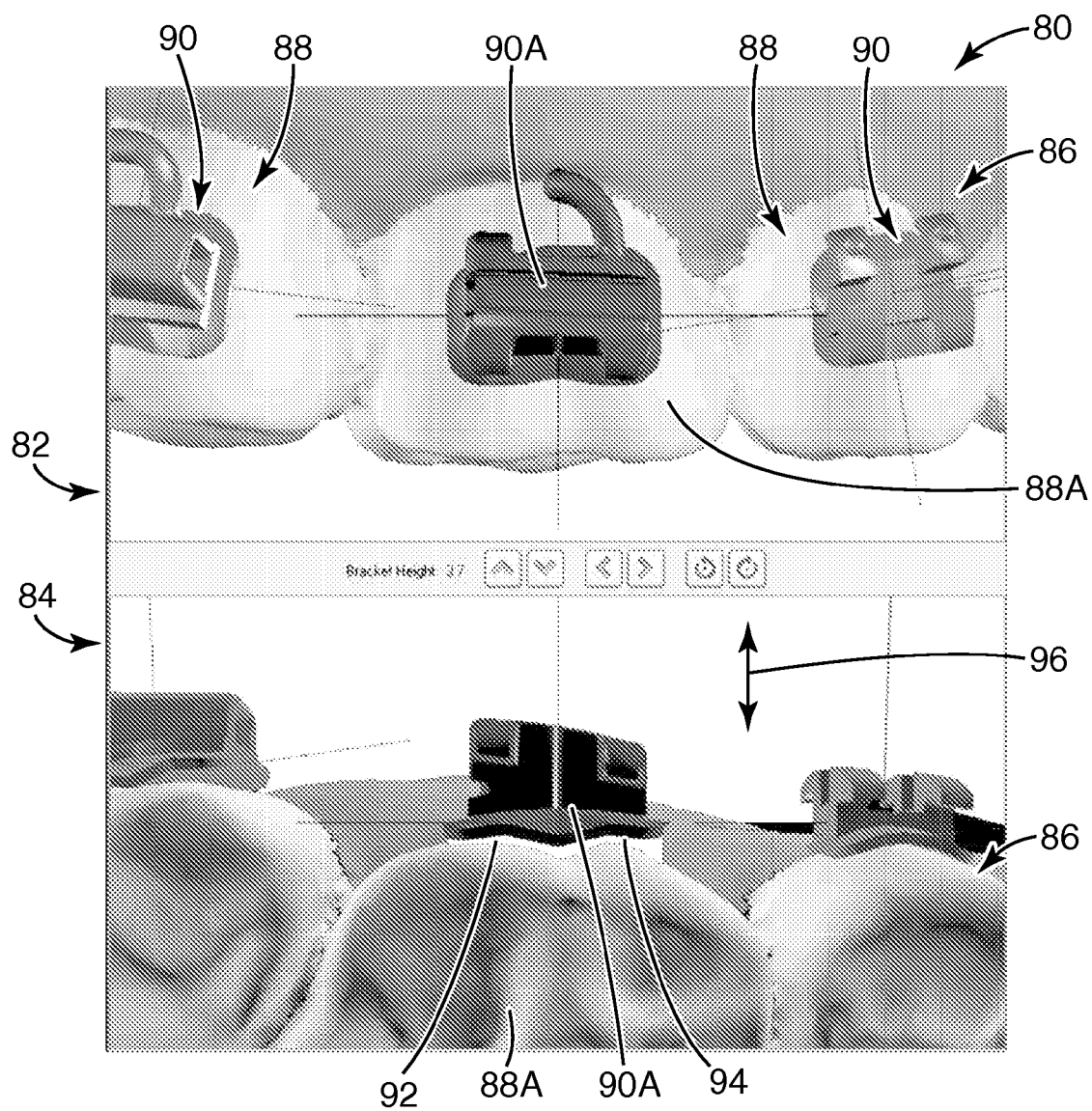
FIG. 5 is a display of an exemplary graphical user interface presented by modeling software of the client computing device shown in FIG. 2.

FIG. 5 is a display diagram of an exemplary GUI 80 presented by modeling software 30 of client computing device 12. GUI 80 includes display areas 82 and 84, which each depict a different view of the digital representation of a part of dental arch 86 of a patient with a 3D modeling environment. Display area 82 illustrates a labial (or facial), looking in a gingival view of dental arch 86, while display area 84 illustrates an occlusal view of dental arch 86 (i.e., illustrates an occlusal surface of dental arch 86, looking generally in a gingival direction).

Dental arch 86 includes a plurality of teeth 88, including tooth 88A. Also depicted in GUI 80 are digital representations of a plurality of brackets 90 attached to teeth 88 of dental arch 86, including bracket 90A attached to tooth 88A. In the embodiment of GUI 80 shown in FIG. 5, practitioner 14 may select one of the brackets 90 in order to view the respective custom base in display area 86. In display area 84, GUI 80 displays a digital presentation of custom base 92 positioned between tooth 88A and bracket 90A. While only custom base 92 is shown in FIG. 5, in other views provided by GUI 80, the custom bases of other brackets 90 may also be displayed.

As FIG. 5 illustrates, one surface of custom base 92 substantially conforms to the contour of labial surface 94 of tooth 88A and a substantially opposite surface of custom base 92 substantially conforms to the surface of bracket 90A facing labial surface 94 of tooth 88A. Because the surface features of labial surface 94 of tooth 88A may differ depending on a particular patient, and custom base 92 substantially conforms to labial surface 94, custom base 92 "customizes" bracket 90A to the particular tooth of a particular patient. Bracket 90A may be a commercially-available bracket stored in inventory, and thus, custom base 92 helps configure a commercially-available bracket for use with a particular patient. Custom base 92 in FIG. 5 is displayed as a uniform color. A uniform color custom base 92 provides a useful tool for determining how well bracket 90A fits on the labial surface of tooth 88A.

In other embodiments, custom base calculation module 36 (FIG. 2) may generate a color-coded thickness map that uses different colors to indicate different thicknesses of custom base 92. In such embodiments, custom base 92 is displayed as two or more colors that define a custom base thickness map. A "thickness" of custom base is measured along the labial-lingual direction, indicated by line 96 in display area 84.

Figure 6A:
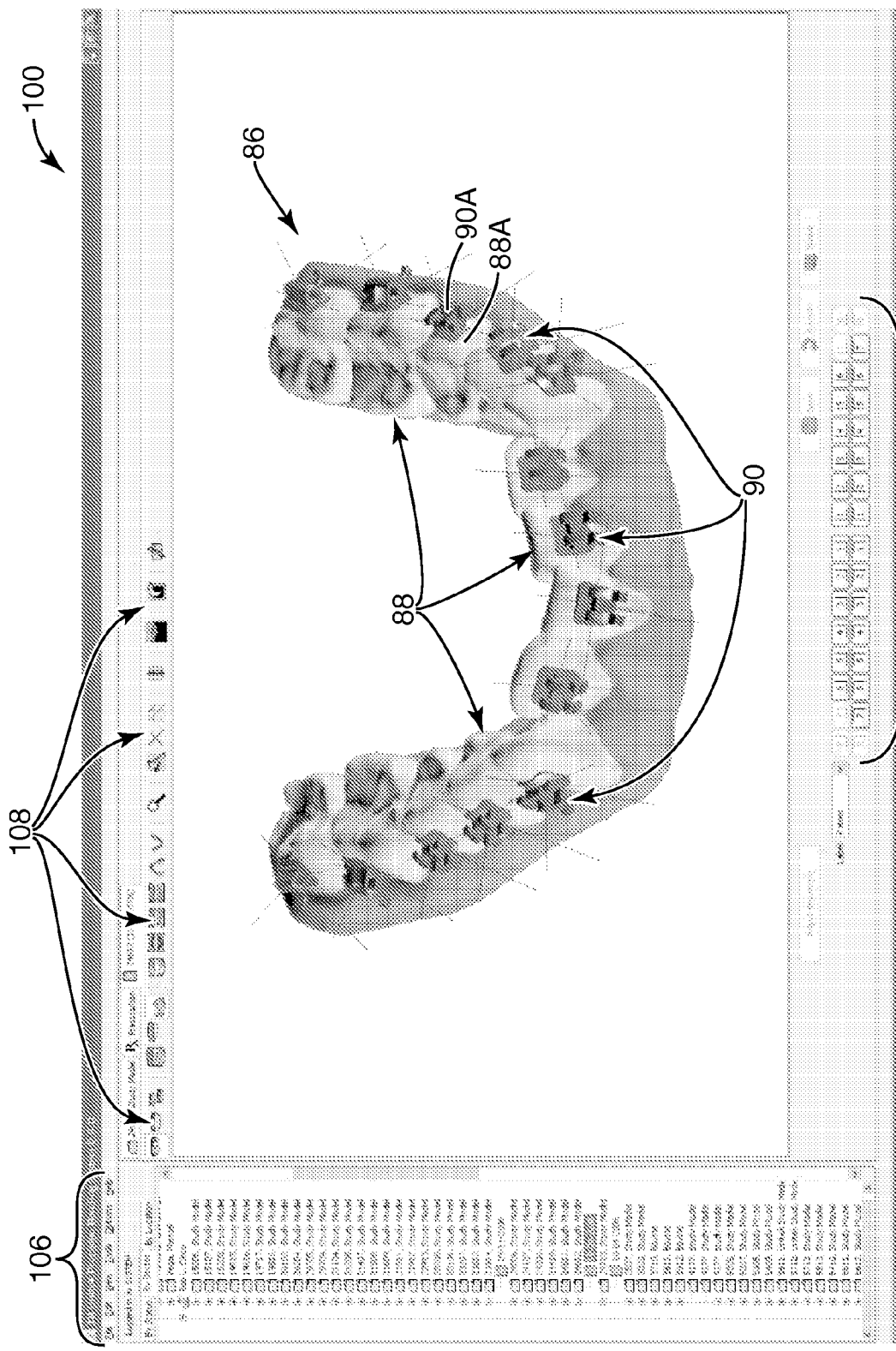
FIGS. 6A-6C illustrate displays of another exemplary graphical user interface presented by the client computing device shown in FIG. 2.
Figure 6B:
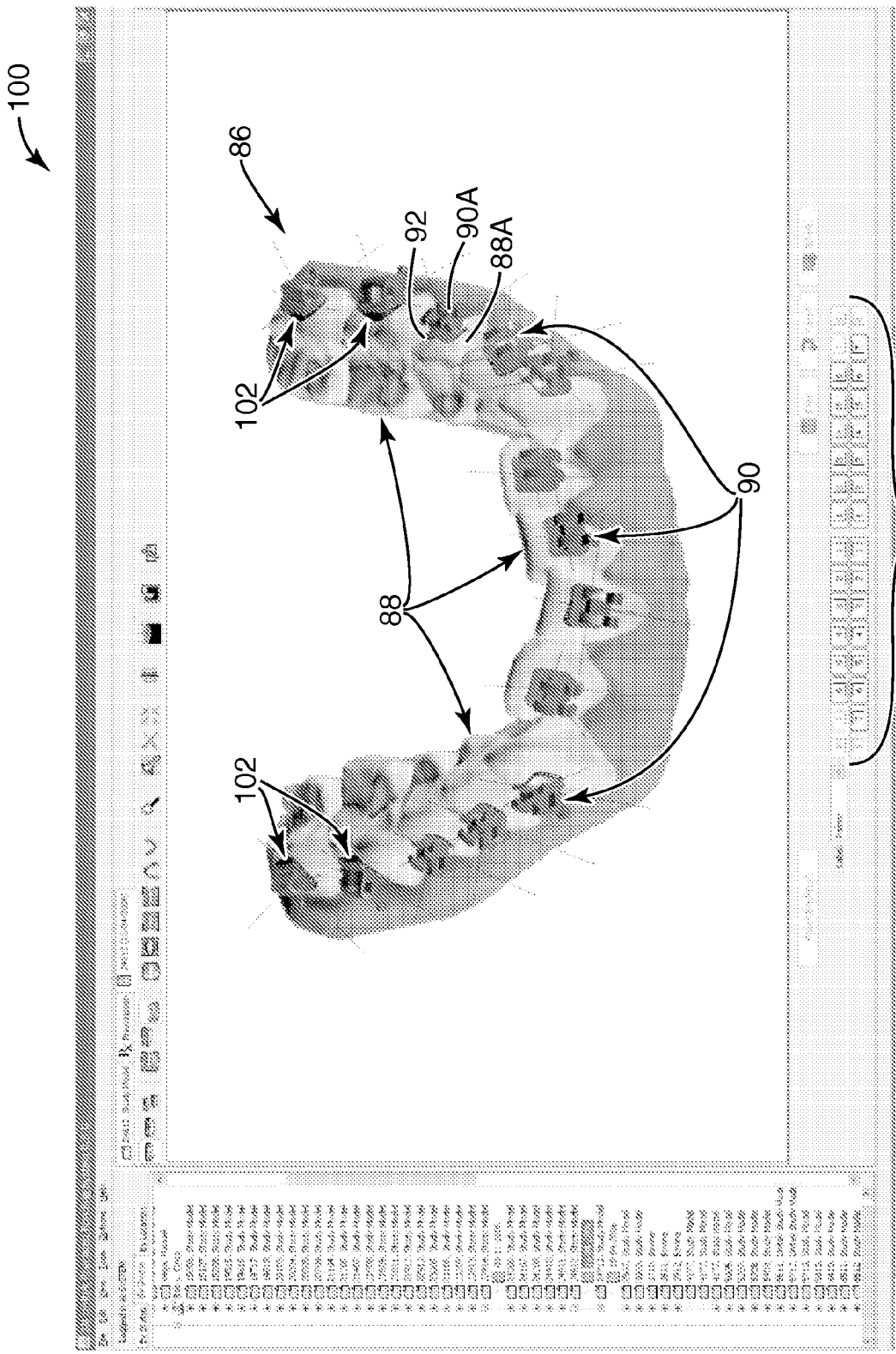

FIGS. 6A and 6B illustrate another example GUI 100 presented by modeling software 30 of client computing device 12. In the embodiment shown in FIGS. 6A and 6B, modeling software 30 is in a full dental arch examination mode in which a full dental arch 86 is shown. of patient 16, where dental arch 86 includes teeth 88. GUI 100 also illustrates brackets 90 attached to respective teeth 88. GUI includes drop-down menus 106 and selection buttons 108. Buttons 108 include, among other things, buttons by which practitioner 14 may choose from any of several views of a patient's dental arch 86.

In FIG. 6A, modeling software 30 is operating in a mode in which custom bases are not shown between each of the teeth 88 and brackets 90. In the display shown in FIG. 6B, modeling software 30 is operating in a mode in which GUI 100 displays custom base 92 and custom bases 102. In some embodiments, practitioner 14 may control modeling software 30 to selectively view the display shown in FIG. 6A or the display shown in FIG. 6B.

In FIG. 6B, custom bases 92 and 102 are displayed as color-coded thickness maps. Brackets 90 obstruct a clear view of the surface of each custom base 92, 102 facing the respective bracket 90. While each custom base 92 and 102 is shown in FIG. 6B, in other embodiments, practitioner 14 may select a particular tooth 88, bracket 90, and custom base 92 or 102 in order to selectively display one or more custom bases 92 or 102. For example, practitioner 14 may select a tooth 88 via object selection menu 104, which identifies particular teeth 88 in dental arch 86 using the Palmer Notation System. In alternate embodiments, object selection menu may identify individual teeth 88, brackets 90, or custom bases 92, 102 by other suitable numbering or labeling systems, such as the Universal Numbering System or the International Numbering System.

Figure 6C:
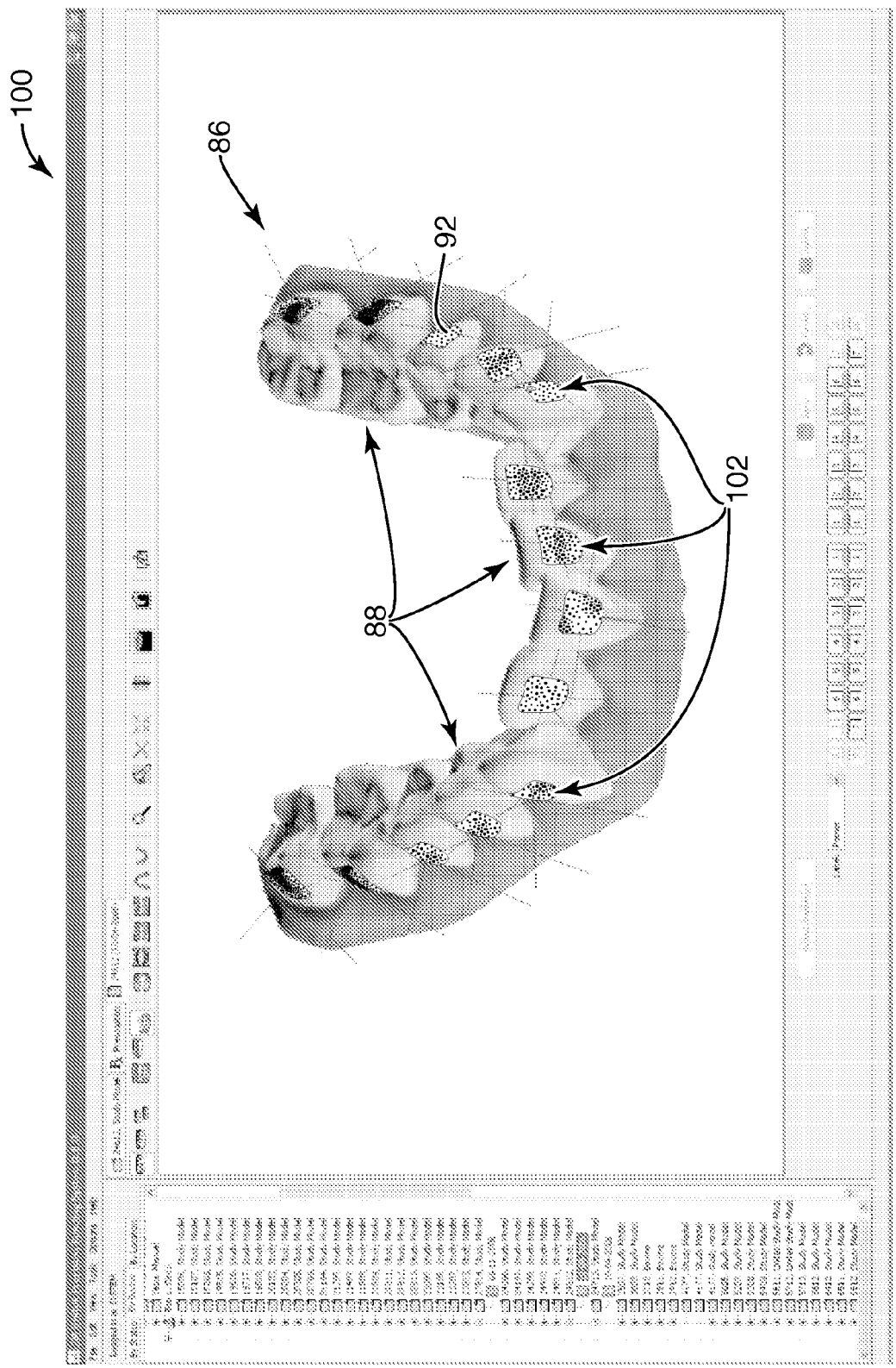

In some modes of operation, practitioner 14 may interact with GUI 100 to disable the display of brackets 90. For example, practitioner 14 may use drop-down menus 106 or operating buttons 108 provided by GUI 100 to select an operating mode in which brackets 90 are displayed as substantially transparent objects or to otherwise disable brackets 90 from being displayed on GUI 100 or from being partially or fully disabled to practitioner 14. An example of a display that does not include brackets 90 is shown in FIG. 6C. Disabling the display of brackets 90 may enable practitioner 14 to view one or more of custom bases 92 and 102 more clearly. If custom base calculation module 36 (FIG. 2) generates a thickness map for each custom base 92 and 102, the removal of brackets 90 from GUI 100 provides an unobstructed view of the thickness maps of custom bases 92 and 102. In FIGS. 6B-C, a thickness of each custom base 92, 102 is shown via gray-scale shading, with darker portions of the shading representing a greater thickness than the lighter portions. In the embodiment shown in FIGS. 6B-6C, there is a relatively smooth, continuous transition between the different shades of gray to represent the substantially continuous contour of custom bases 92, 102. However, discrete shades of gray may also be used. As described above, in other embodiments, other thickness indicators may be used, such as, but not limited to, color-coded maps, contour maps or text boxes that provide a thickness value.

Figure 7A:
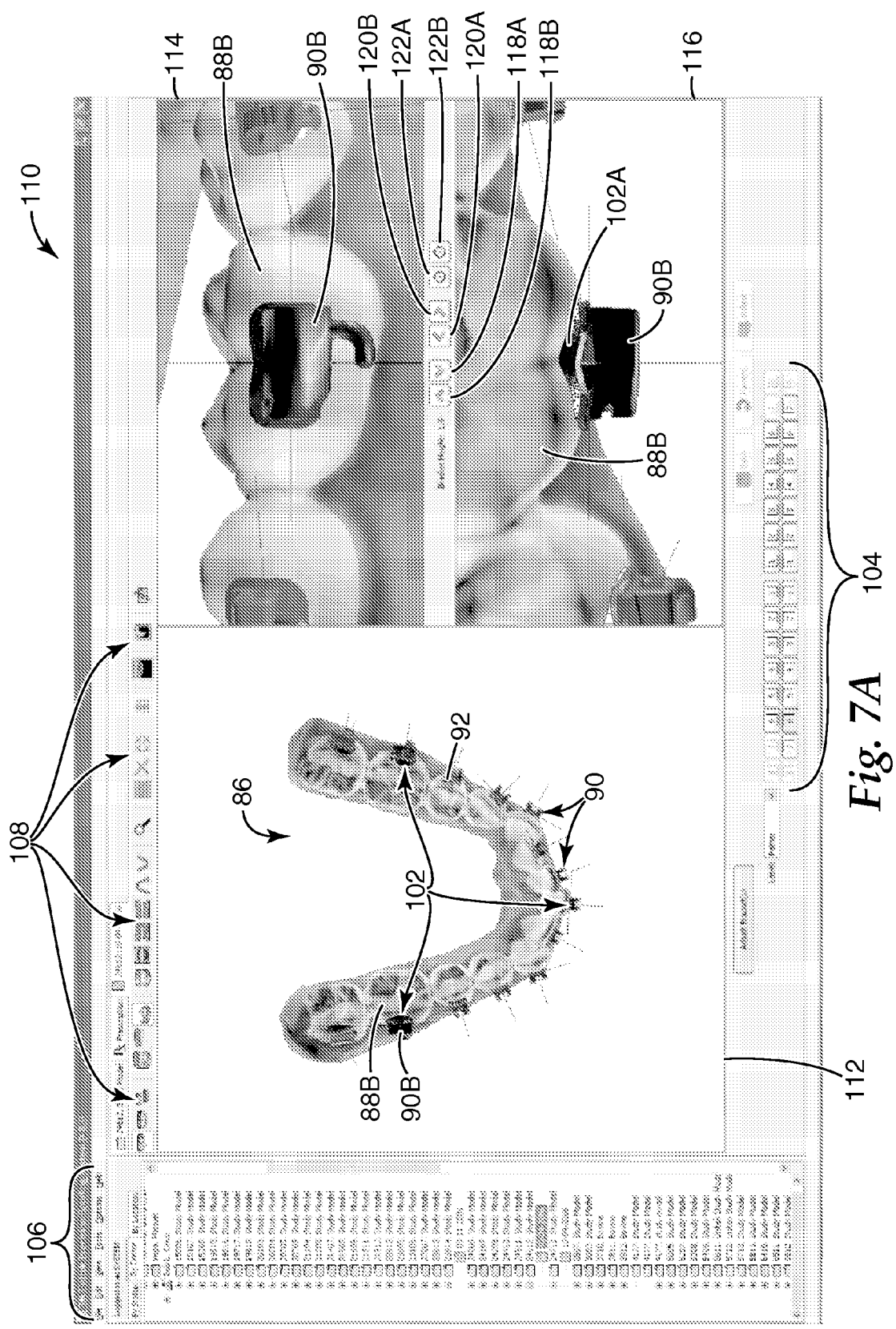
FIGS. 7A and 7B illustrate displays of another exemplary graphical user interface presented by the client computing device shown in FIG. 2.
Figure 7B:
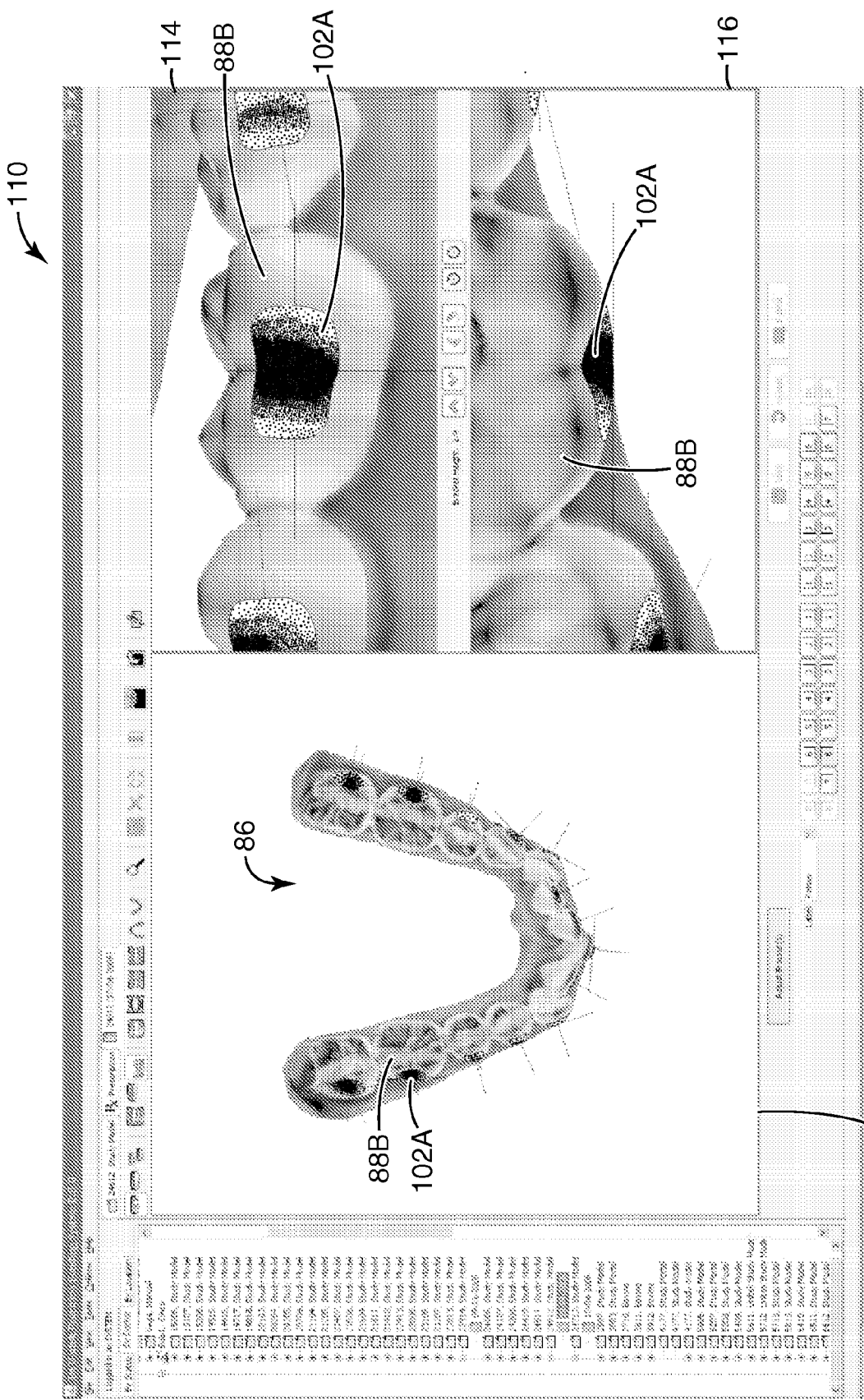

FIGS. 7A and 7B illustrate another GUI 110 that may be presented by modeling software 30 of client computing device 12 (FIG. 2). In FIGS. 7A-B, a thickness of each custom base 92, 102 is shown via gray-scale shading, with darker portions of the shading representing a greater thickness than the lighter portions. Again, in other embodiments, other thickness indicators may be used, such as, but not limited to, color-coded maps, contour maps or text boxes that provide a thickness value.

Just as with GUI 100 of FIGS. 6A-6C, GUI 110 allows practitioner 14 to choose from any of several views of a patient's dental arch 86 via pull-down menus 106 and/or selection buttons 108. In the embodiment of GUI 110 illustrated in FIGS. 7A and 7B, GUI 110 simultaneously displays three views. In particular, display area 112 depicts a full dental arch 86, display area 112 depicts an enlarged view of a portion of dental arch 86 from a labial perspective, and display area 114 depicts a view of the portion of dental arch 86 shown in display area 112, but from an occlusal perspective. In other embodiments, GUI 110 may display any suitable number of views of dental arch 86.

Display area 112 indicates that tooth 88B of dental arch 86 and the respective bracket 90B are selected for viewing in display areas 114, 116. For example, GUI 110 may indicate which tooth 88 and/or bracket 90 is selected by visually distinguishing the selected tooth 88 and/or bracket 90, such as by displaying the selected tooth 88 and/or bracket 90 in another color. In the embodiment shown in FIG. 7A, practitioner 14 may select tooth 88B and/or bracket 90B by directly selecting the digital representation of tooth 88B and/or bracket 90B with a mouse, another peripheral pointing device or by indirectly selecting tooth 88B and/or bracket 90B via menu 104 or pull-down menu 106. Also visible in display area 112 are custom bases 92, 102, which are color-coded to visually indicate the variation in thickness that results from the particular positioning of respective brackets 90 relative to the respective teeth 88.

Display area 114 illustrates a buccal view of selected tooth 88B and bracket 90B, as well as a portion of adjacent teeth 88 and brackets 90. The custom base for bracket 90B is not visible from the labial view shown in display area 114. However, display area 116, which illustrates an occlusal view of tooth 88B, illustrates custom base 102A in addition to the selected tooth 88B and bracket 90B. GUI 110 provides practitioner 14 with an interface for viewing individual teeth 88 of dental arch 86 as well as a custom base 92, 102 that results from a position of a bracket 90 relative to a respective tooth 88.

Practitioner 14 may also select a view, such as by a drop down menu 106, in which brackets 90 are displayed as substantially transparent objects or not displayed at all in order to provide practitioner 14 with an interface in which custom bases 102 are more visible. FIG. 7B illustrates GUI 110 in which brackets 90 are displayed as substantially transparent objects. Practitioner 14 may switch between the views shown in FIGS. 7A and 7B. The view shown in FIG. 7A may be useful for visualizing bracket 90B on tooth 88B, and the view shown in FIG. 7B without brackets 90 may be useful for visualizing the thickness distribution of custom bases 102.

A bracket adjustment mode of modeling software is shown in GUI 110 of FIGS. 7A and 7B. In the bracket adjustment mode, practitioner 14 may select a particular bracket and adjust the position of the bracket, e.g., by adjusting the translation or rotation of the bracket, by refitting the bracket on the tooth or by replacing the bracket with another bracket. Practitioner 14 may adjust a height of one of brackets 90 by selecting the bracket (e.g., using menu 104 or by selecting the digital representation of the desired bracket within one of windows 112, 114 or 116) and dragging the selected bracket in the gingival or occlusal directions, or adjust a mesial-distal position of one of brackets 90 by selecting the bracket and dragging the selected bracket in the mesial direction or distal direction. Practitioner 14 may also manipulate the selected bracket within the 3D environment to induce the desired rotational position relative to a tooth 88 with a peripheral pointing device. Alternatively, practitioner 14 may use buttons 118A,B to incrementally move the selected bracket in a gingival or occlusal direction, respectively, buttons 120A, B to incrementally move the selected bracket in the mesial or distal directions, and/or buttons 122A, B to incrementally adjust the rotational position of the selected bracket. Each click of button 118A-B, 120A-B, and 122A-B is typically associated with a discrete movement of the selected bracket.

With each of GUIs 80 (FIG. 5), 100 (FIGS. 6A-6C), and 110 (FIG. 7), orthodontic appliance control module 34 and custom base calculation module 36 (FIG. 2) enable practitioner 14 to interactively develop a treatment plan and corresponding orthodontic prescription that will result in a desired final occlusion using the virtual 3D model of the patient's dentition presented on the respective GUI. Each GUI 80, 100, 110 may present the crowns and/or the roots or gingiva of the teeth to the practitioner 14 for visualization and interactive movement of teeth 88 and/or brackets 90 in order to develop the treatment plan. For example, practitioner 14 may view custom bases 102 in either the GUI 110 shown in FIG. 7A or 7B in order to determine whether the position of bracket 90B currently displayed (whether or not bracket 90B itself is displayed) is suitable for tooth 88B.

If practitioner 14 determines that the custom base 102A distribution is unacceptable, e.g., a thickness of custom base 102A at one or more portions, such as at a mesial portion, exceeds a threshold, practitioner 14 may manually reposition bracket 90B or implement a repositioning algorithm that automatically repositions bracket 90B. Practitioner 14 may manually reposition bracket 90B using adjustment buttons 112A-B, 114A-B, and 116A-B. Buttons 112A-B move bracket 90B in an occlusal-gingival direction, while buttons 114A-B move bracket 90B in a mesial-distal direction and buttons 116A-B adjust the rotational orientation of bracket 90B. Alternatively, practitioner 14 may reposition bracket 90B by clicking on bracket 90B with a mouse or another peripheral pointing device and dragging bracket 90B to the desired position, which may include the rotational orientation.

Rather than repositioning bracket 90B relative to tooth 88B in order to achieve a better fit between bracket 90B, e.g., to achieve a more uniform custom base 102A distribution, practitioner 14 may select another bracket to apply on tooth 88B within the 3D environment via drop down menus 106. After orthodontic appliance control module 34 (FIG. 2) places the new bracket within the 3D environment relative to tooth 88B, custom base calculation module 36 and rendering engine 38 may render a custom base and a custom base thickness map for the new bracket. Practitioner 14 may subsequently determine whether the new bracket provides a better fit for tooth 88B based on the resulting custom base. Practitioner 14 may also interact with GUI 110 to view the fit of the other brackets 90 relative to the respective teeth 88 and reposition other brackets 90 if necessary or desired.

In one or more exemplary embodiments, various functions described in this disclosure may be implemented in hardware, software, and/or firmware, or any combination thereof. If implemented in hardware, the functions may be implemented in a processor. A processor may include one or more microprocessors, microcontrollers, digital signal processors (DSPs), application specific integrated circuits (ASICs), field programmable gate arrays (FPGAs), or the like. Such components may reside within a computing system or other systems.

If implemented in software, the functions may be stored as one or more instructions or code on a computer-readable medium. Computer-readable media includes computer storage media. A storage medium may be any available media that can be accessed by a computer. By way of example, and not limitation, such computer-readable media can comprise random-access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Storage media may comprise computer program products. Disk and disc, as used herein, includes compact disc (CD), laser disc, optical disc, DVD optical discs, floppy disk and blu-ray disc where disks usually reproduce data magnetically, while discs reproduce data optically with lasers. Combinations of the above should also be included within the scope of computer-readable media.

A digital representation of a coupling matrix is useful for applications other than determining whether the displayed bracket provides a satisfactory fit for a patient. For example, in other embodiments, modeling software 30 of computing device 12, which renders a digital representation of a coupling matrix for a particular orthodontic appliance and tooth, may also be useful for forming the actual coupling matrix. As one example, in embodiments in which the coupling matrix is defined by a material that is integral with the orthodontic appliance, the digital data from modeling software 30 that defines the shape and size of the coupling matrix may be used to control the machining of the appliance to define the coupling matrix. For example, modeling software 30 may provide information relating to the configuration (e.g., shape and size) of the digital representation of the coupling matrix to a device that forms a graphite electrode for use with an electrical discharge machining (EDM) process. The face of the electrode defines the surface of the coupling matrix that mates with the surface of the patient's tooth.

As another example, in embodiments in which the coupling matrix is defined by an adhesive or another dispensable coupling matrix material, the digital representation of the coupling matrix may be used to guide an apparatus that automatically dispenses the adhesive. In this way, the digital representation of the coupling matrix may be used to form the actual coupling matrix. Automatically dispensing the adhesive based on the volume and thickness distribution of the digital representation of the coupling matrix provided by modeling software 30 may help reduce or eliminate flash, and reduce or eliminate the practitioner's time spent in removing the flash. As previously described, flash generally refers to excess coupling matrix material that, for example, flashes out from the perimeter of the orthodontic appliance when the appliance is applied to the tooth by the practitioner, a calibrated bracket placement robot, or using a 3D printed model incorporating bracket placement guides. Flash removal may be a time consuming process because of the manual dexterity, skill, and patience required. In addition, the automatic dispensing of the coupling matrix material may help limit the amount of coupling matrix material that is wasted.

The digital representation of the coupling matrix may also be used to fabricate the coupling matrix in the desired configuration, e.g., using various Solid Freeform Fabrication (SFF) techniques, such as 3D printing. Computing device 12 may control the fabrication (or formation) of the coupling matrix based on the size and geometry of the digital representation of the coupling matrix, or computing device 12 may provide the size and geometry information to another device that controls the fabrication apparatus.

The fabricated coupling matrices may then be applied to the appliance, the respective one or more teeth, or both using a low-viscosity primer (such as Transbond XT Primer available from 3M Unitek of Monrovia, Calif.). In some embodiments, the fabricated coupling matrices may incorporate special appendages or registration features to facilitate proper alignment with features on the appliances or guides that are incorporated into the 3D physical model of the patient's teeth, to help ensure a proper fit between the tooth and the coupling matrix, the appliance and the coupling matrix, or both. U.S. patent application Ser. No. 11/689,869, entitled, "METHODS AND ASSEMBLIES FOR MAKING AN ORTHODONTIC BONDING TRAY USING RAPID PROTOTYPING," which was previously incorporated by reference, describes an example of suitable guides that may be incorporated into a 3D model of the patient's teeth.

In other embodiments, a coupling matrix may be fabricated along with the 3D physical model of the patient's teeth in an indirect bonding technique. For example, a first material that is soluble in a first solvent may be used as a general support material for the 3D model of the patient's teeth (e.g., for supporting undercuts in geometry), and a second material that is soluble in a second solvent, but not the first, may be used in the interface between the coupling matrix and the physical model of the patient's teeth. After an orthodontic appliance is bonded to the coupling matrix with a primer, and the appliance is fixed in its desired position by an indirect bonding tray formed over the appliances and physical model, the second solvent may be used to dissolve the second material, thereby releasing the coupling matrix from the model. Other techniques, including mechanical intervention, may also be used to release the coupling matrix from the physical model of the patient's teeth.

Various embodiments of the invention have been described. These and other embodiments are within the scope of the following claims.

The invention claimed is:

1. A computer-implemented method comprising:
rendering a digital representation of at least a portion of a tooth within a three-dimensional (3D) environment;
determining a position of a digital representation of at least a portion of an orthodontic appliance relative to the digital representation of the tooth within the 3D environment;
determining a thickness of at least a portion of a coupling matrix;
rendering a digital representation of the coupling matrix within the 3D environment based on the position of the orthodontic appliance, wherein rendering the digital representation of the coupling matrix within the 3D environment comprises presenting a user interface that visually displays the digital representation of the coupling matrix within the 3D environment; and
wherein rendering the coupling matrix includes rendering a color-coded thickness map based on the determined thickness, wherein the color-coding includes at least two different colors representing respective thickness ranges.

2. The method of claim 1, wherein the thickness ranges indicate a deviation from a baseline thickness.

3. The method of claim 2, wherein the baseline thickness comprises a norm thickness associated with at least one orthodontic practitioner.

4. The method of claim 2, wherein the baseline thickness comprises a norm thickness associated with at least one set of orthodontic appliances.

5. The method of claim 2, wherein the baseline thickness comprises a threshold thickness value to achieve a sufficient bond between the orthodontic appliance and tooth.

6. The method of claim 1, wherein the thickness ranges each indicate a respective gross thickness measurement.

7. A computer-implemented method comprising:
rendering a digital representation of at least a portion of a tooth within a three-dimensional (3D) environment;
determining a position of a digital representation of at least a portion of an orthodontic appliance relative to the digital representation of the tooth within the 3D environment;
determining a thickness of at least a portion of a coupling matrix;
rendering a digital representation of the coupling matrix within the 3D environment based on the position of the orthodontic appliance, wherein rendering the digital representation of the coupling matrix within the 3D environment comprises presenting a user interface that visually displays the digital representation of the coupling matrix within the 3D environment;
further comprising determining a volume of the coupling matrix; and
wherein determining the volume of the coupling matrix comprises:
subdividing the digital representation of the coupling matrix into a plurality of substantially equal-sized columns; and
determining a volume of each of the plurality of columns based on a thickness of each of the columns.

8. The method of claim 7, further comprising:
assigning each of the plurality of columns a color based on a length of the respective column, wherein the length is measured along a substantially similar direction as the thickness of the coupling matrix; and
displaying the columns in the assigned color.

9. A system comprising:
a computing device; and
modeling software executing on the computing device, wherein the modeling software comprises:
a rendering engine that renders a digital representation of at least a portion of a tooth and at least a portion of a coupling matrix within a three-dimensional (3D) environment by at least presenting a user interface that visually displays the digital representation of the at least the portion of the tooth and the at least the portion of the coupling matrix within the 3D environment;
an orthodontic appliance control module to automatically calculate a position of an orthodontic appliance relative to the digital representation of the tooth within the 3D environment;
a coupling matrix calculation module to determine a thickness of at least a portion of the coupling matrix based on the orthodontic appliance position; and wherein the thickness map is color-coded to differentiate between at least two different thickness ranges.

10. A system comprising:

a computing device; and modeling software executing on the computing device, wherein the modeling software comprises:
- a rendering engine that renders a digital representation of at least a portion of a tooth and at least a portion of a coupling matrix within a three-dimensional (3D) environment by at least presenting a user interface that visually displays the digital representation of the at least the portion of the tooth and the at least the portion of the coupling matrix within the 3D environment;
- an orthodontic appliance control module to automatically calculate a position of an orthodontic appliance relative to the digital representation of the tooth within the 3D environment;
- a coupling matrix calculation module to determine a thickness of at least a portion of the coupling matrix based on the orthodontic appliance position; and
- wherein the thickness map is color-coded to indicate a deviation from a baseline thickness.

* * * * *